United States Patent
Bodduluri et al.

(10) Patent No.: US 7,922,688 B2
(45) Date of Patent: Apr. 12, 2011

(54) AUTOMATED DELIVERY OF A THERAPEUTIC OR COSMETIC SUBSTANCE TO CUTANEOUS, SUBCUTANEOUS AND INTRAMUSCULAR TISSUE REGIONS

(75) Inventors: Mohan Bodduluri, Palo Alto, CA (US); Miguel G. Canales, Los Altos, CA (US); James W. McCollum, Coronado, CA (US); Philip L. Gildenberg, Houston, TX (US); Douglas E. Kelly, Palo Alto, CA (US); Jeffrey Bird, Menlo Park, CA (US); Frederic H. Moll, Los Altos, CA (US)

(73) Assignee: Restoration Robotics, Inc., Mountain View, CA (US)

( * ) Notice: Subject to any disclaimer, the term of this patent is extended or adjusted under 35 U.S.C. 154(b) by 721 days.

(21) Appl. No.: 11/621,087

(22) Filed: Jan. 8, 2007

(65) Prior Publication Data
US 2008/0167674 A1 Jul. 10, 2008

(51) Int. Cl.
*A61M 31/00* (2006.01)
*A61M 5/20* (2006.01)
*A61B 17/34* (2006.01)

(52) U.S. Cl. .................. 604/62; 604/156; 606/187
(58) Field of Classification Search .............. 604/57, 604/59–65, 67, 156, 157, 246; 606/131, 606/133, 185, 187
See application file for complete search history.

(56) References Cited

U.S. PATENT DOCUMENTS

| 4,807,163 | A | 2/1989 | Gibbons |
| 5,540,657 | A | 7/1996 | Kurjan et al. |
| 5,562,613 | A | 10/1996 | Kaldany |
| 5,827,217 | A | 10/1998 | Silver et al. |
| 5,851,831 | A | 12/1998 | Inamatsu et al. |
| 5,865,744 | A | 2/1999 | Lemelson |
| 6,488,636 | B2 | 12/2002 | Bryan et al. |
| 6,585,746 | B2 | 7/2003 | Gildenberg |
| 6,639,051 | B2 | 10/2003 | Wang |
| 6,884,427 | B1 | 4/2005 | Barrows |
| 6,973,931 | B1 | 12/2005 | King |

(Continued)

FOREIGN PATENT DOCUMENTS

DE 10249786 A1 5/2004

(Continued)

OTHER PUBLICATIONS

PCT International Search Report and Written Opinion of the International Searching Authority for PCT/US2007/088975, Applicant, Restoration Robotics, Inc., Forms PCT/ISA/210,220 and 237, mailed Nov. 13, 2008. (19 Pages).

(Continued)

*Primary Examiner* — Nicholas D Lucchesi
*Assistant Examiner* — Nathan R Price
(74) *Attorney, Agent, or Firm* — Lena I. Vinitskaya; David T. Burse; Sharon Upham

(57) ABSTRACT

Automated systems and methods for delivery of a therapeutic or cosmetic substance into cutaneous, subcutaneous or intramuscular tissue, wherein an automated (e.g., robotic) arm is maneuvered to position a delivery device proximate a targeted location (e.g., an existing hair follicle, a location for implanting a skin filler, or a location for intradermal tattoo ink injection) on a patient's skin surface; and a substantially automated process is used to cause the delivery device to puncture the skin surface and penetrate to a desired depth into the tissue at the targeted location, and deliver the substance therein.

31 Claims, 9 Drawing Sheets

U.S. PATENT DOCUMENTS

| | | |
|---|---|---|
| 7,083,611 B2 | 8/2006 | Lemchen |
| 7,094,569 B2 | 8/2006 | Kim et al. |
| 2001/0027293 A1 | 10/2001 | Joshi |
| 2002/0133149 A1 | 9/2002 | Bessette |
| 2003/0120298 A1* | 6/2003 | Gildenberg .......... 606/187 |
| 2003/0198646 A1 | 10/2003 | Stenn |
| 2005/0147652 A1 | 7/2005 | Atkins et al. |
| 2005/0154431 A1 | 7/2005 | Quistgaard et al. |
| 2007/0078466 A1 | 4/2007 | Bodduluri et al. |
| 2007/0078475 A1 | 4/2007 | Bodduluri et al. |
| 2007/0106307 A1 | 5/2007 | Bodduluri et al. |
| 2007/0212335 A1 | 9/2007 | Hantash et al. |
| 2008/0033455 A1 | 2/2008 | Rassman et al. |
| 2008/0051816 A1* | 2/2008 | Pak et al. .......... 606/187 |
| 2008/0154247 A1 | 6/2008 | Dallarosa et al. |
| 2008/0247637 A1 | 10/2008 | Gildenberg |
| 2009/0230269 A1 | 9/2009 | Dallarosa |

FOREIGN PATENT DOCUMENTS

| | | |
|---|---|---|
| WO | 9825666 A1 | 6/1998 |
| WO | 00/09184 | 2/2000 |
| WO | WO 00/49138 A2 | 8/2000 |
| WO | WO 01/11011 A2 | 2/2001 |
| WO | 0149360 | 7/2001 |
| WO | WO 01/74164 A1 | 10/2001 |
| WO | 03039596 A1 | 5/2003 |
| WO | 03068248 | 8/2003 |
| WO | 2004044188 | 5/2004 |
| WO | 2007041267 | 4/2007 |
| WO | 2007092929 | 8/2007 |

OTHER PUBLICATIONS

Niki Passath, "Kurt, the tattoo robot", Nov. 26, 2002, Website printout <http://www.we-make-money-not-art.com/archives/2005/09/yesterday-at-th.php>, pages printed on Sep. 3, 2008 (2 pages).

PCT Invitation to pay additional fees of the International Search Authority for PCT/US2007/088975, Applicant Restoration Robotics, Inc., Form PCT/ISA/206 dated Aug. 18, 2008, and Annex to form PCT/ISA/2006 (8 pages).

Howstuffworks "How Tattoo Removal Works," web page accessed on Jan. 7, 2008, http://people.howstuffworks.com/tattoo-removal.htm/printable (4 pages).

"Tattoo Machine," Tattoo machine—Wikipedia, web page accessed on Apr. 5, 2007, http://wikipedia.org/wiki/Tattoo_machine (5 pages).

Howstuffworks "How Tattoos Work," Tracy V. Wilson, web page accessed on Nov. 30, 2007, http://people.howstuffworks.com/tattoo.htm (5 pages).

Paus & Cotsarelis, "The Biology Of Hair Follicles", New England Journal of Medicine, 341(7), Aug. 12, 1999, pp. 491-497, downloaded from www.nejm.org. (7 pages).

J.G. Toma et al., "Isolation of Multipotent Adult Stem Cells From the Dermis of Mammalian Skin," Nature Cell Biology, vol. 3, Sep. 2001, pp. 778-784, http://cellbio.nature.com. (7 pages).

http://en.wikipedia.org/wiki/Tattoo_machine, "Tattoo Machine", entry last modified on Mar. 29, 2007, downloaded on Apr. 5, 2007, (2 pages).

http://en.wikipedia.org/wiki/Melanocyte, "Melanocyte", entry last modified on Mar. 29, 2007, downloaded on Apr. 5, 2007, (3 pages).

Jennifer Y. Lin & David E. Fisher, "Melanocyte biology and skin pigmentation", Nature vol. 445, Feb. 22, 2007, Nature Publishing Group.

Second Preliminary Amendment filed Jun. 5, 2009 in relation to U.S. Appl. No. 11/380,911, published as US 2007/0106307, (8 Pages).

PCT International Search Report for PCT/US2007/088971, Applicant Restoration Robotics, Inc., Forms PCT/ISA/210,220, dated Aug. 26, 2008 (8 pages).

PCT International Written Opinion for PCT/US2007/088971, Applicant Restoration Robotics, Inc., Forms PCT/ISA/237, dated Aug. 26, 2008 (11 pages).

* cited by examiner

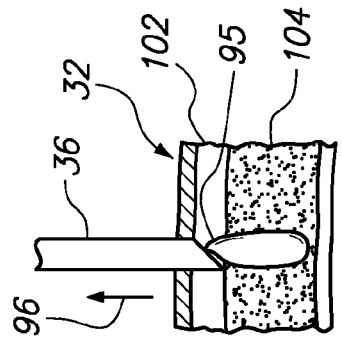
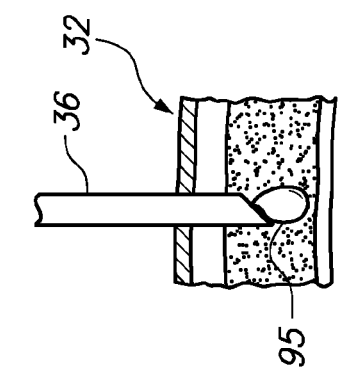
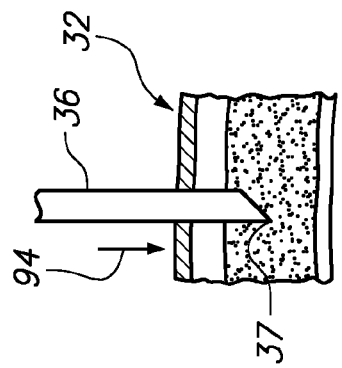
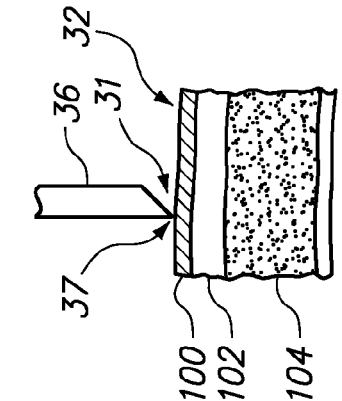
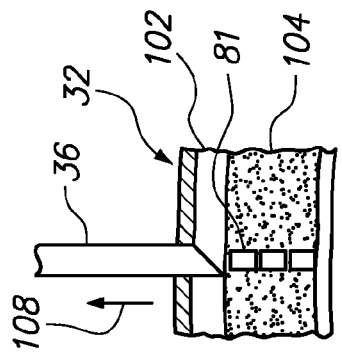
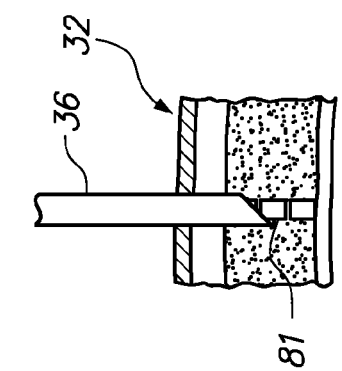
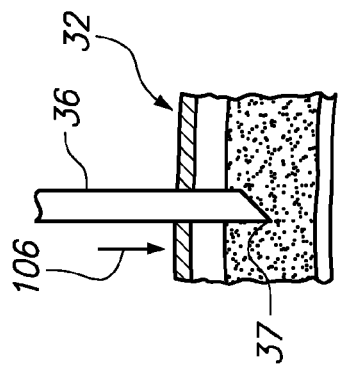
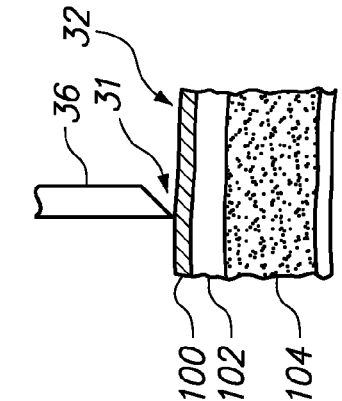

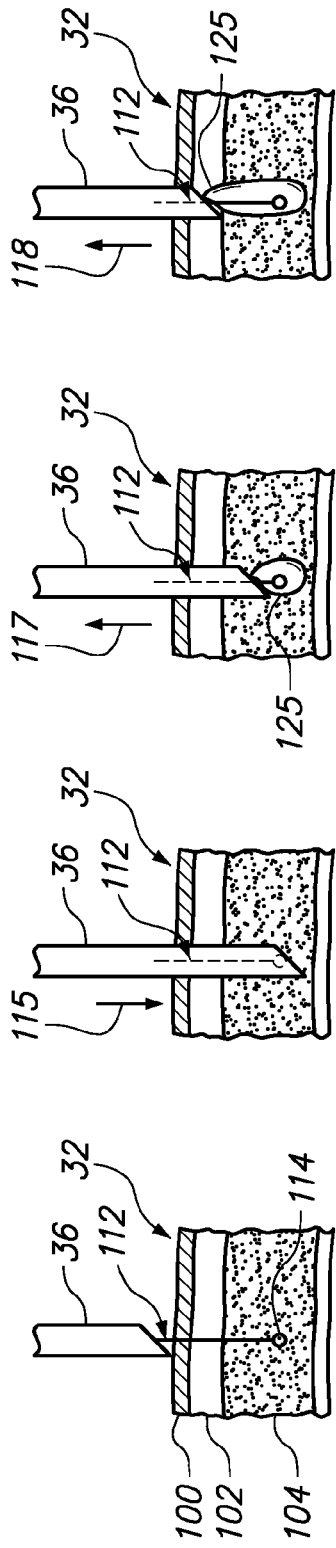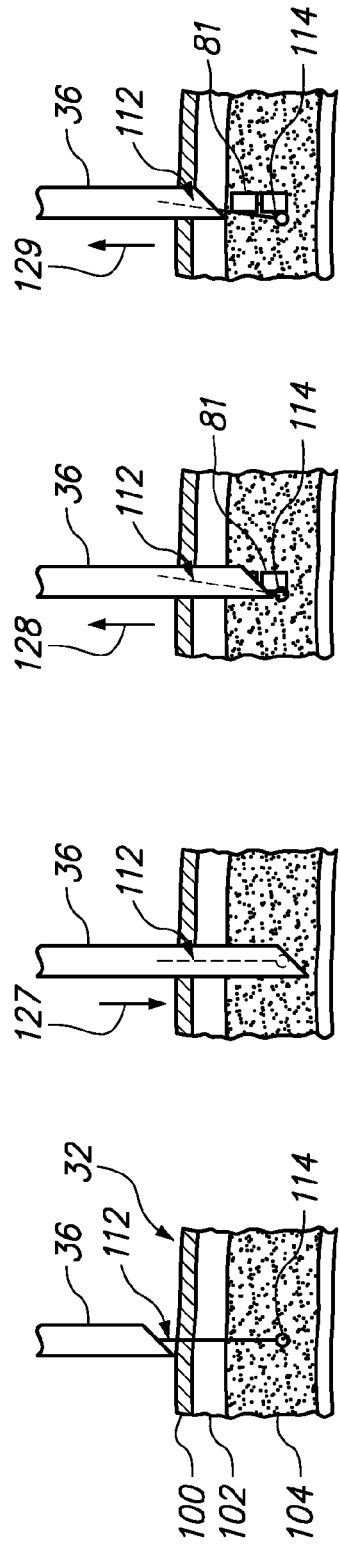

AUTOMATED DELIVERY OF A THERAPEUTIC OR COSMETIC SUBSTANCE TO CUTANEOUS, SUBCUTANEOUS AND INTRAMUSCULAR TISSUE REGIONS

FIELD OF INVENTION

This invention relates generally to automated (e.g., robotic) systems and methods employing such automated systems for controlled delivery of a therapeutic or cosmetic substance into or through the skin layers to targeted cutaneous, subcutaneous and intramuscular tissue regions.

BACKGROUND

Numerous procedures are currently performed or are under consideration for both therapeutic and cosmetic (both aesthetic and reconstructive) purposes in which a temporary or permanent substance is injected or otherwise implanted into or through the skin layers to targeted cutaneous, subcutaneous and intramuscular tissue regions. By way of example, procedures that implant collagen-emitting fibroblasts, hyaluronic acid products and/or muscle inhibitors (e.g., Botox®) for facial or body rejuvenation or reconstruction involve making a number of injections of minute amounts of substances into targeted intradermal and subcutaneous tissues (e.g., between the epidermis and the dermis; within the dermis, or into the subcutaneous fat and intramuscular layers). Another example is the injection of fat cells into a subcutaneous fat layer for facial or body "lipo-contouring".

Such procedures are often labor intensive, and require a number of skin-piercing, i.e., "transcutaneous" injections, with each injection delivering a relatively small quantity of a substance to a given depth below the skin surface, and in a given pattern, into the targeted tissue. The intradermal injection of pigments (e.g., for tattoos) is another example of a well-known, labor intensive process in which pigment ink is repeatedly injected into the dermis to form a desired (and stable) pattern that is visible through the epidermis. By way of yet another example, it has been proposed to inject stem cells to grow hair, e.g., hair follicular cells or inductive dermal papilla cells, into the areas of the scalp in which the patient's natural hair follicular cells are no longer growing.

One well-known transcutaneous procedure is hair transplantation, which typically involves (in the case of male pattern baldness) harvesting donor hair follicles (or grafts containing multiple follicles) from the side and back fringe areas of the patient's scalp, and implanting the hair follicles or grafts in a bald "recipient" area on the top and top-front of the scalp. "Follicular units" are naturally occurring aggregates of 1-3 (and much less commonly, 4-5) closely spaced hair follicles that are distributed randomly over the surface of the scalp. Until recently, both the harvesting and implantation of follicular units has been performed manually, and can be a very laborious and painstaking procedure.

Automated (e.g. robotic) systems and methods for harvesting and implanting hair follicular units have been invented and are currently under commercial development by Restoration Robotics, Inc., of Mountain View, Calif. (assignee of the present application). In particular, U.S. Pat. No. 6,585,746 to Gildenberg[, which is incorporated herein by reference in its entirety,] discloses a hair transplantation system utilizing a robotic system, including a robotic arm and a hair follicle introducer associated with the robotic arm. A video system is used to produce a three-dimensional virtual image of the patient's scalp, which is used to plan the scalp locations that are to receive hair grafts implanted by the follicle introducer under the control of the robotic arm.

U.S. patent application Ser. Nos. 11/380,903, filed Apr. 28, 2006, and 11/421,438, filed May 31, 2006 (collectively "Bodduluri"), which are incorporated herein by reference in their entirety, disclose and describe an automated system for transplanting hair follicular units, which employs a multi-part tool assembly carried on a distal end of a robotic arm. The tool assembly is independently controllable relative to the robotic arm, and includes an inner, "harvesting" cannula with a longitudinal axis that is automatically aligned (under image-guidance) with a selected follicular unit to be harvested from a donor area of a body surface, and then advanced relative to the body surface so that an open, tissue coring distal end of the harvesting cannula penetrates the body surface surrounding the selected follicular unit to a depth sufficient to substantially encapsulate the follicular unit. The harvesting cannula is then withdrawn from the body surface with the follicular unit engaged by and retained in an interior lumen thereof. An outer, "implanting" cannula is disposed coaxially over (and moveable relative to) the harvesting cannula, wherein a tissue piercing distal end of the implanting cannula is used to puncture a recipient area of the body surface and form an implantation cavity, with the follicular unit displaced from the harvesting cannula lumen into the implantation cavity.

While these advances with regard to hair transplantation are very promising for reducing if not eliminating the need for such procedures to be performed manually, there remains a need for similar automated apparatus for performing other procedures involving the transcutaneous delivery of therapeutic and cosmetic substances to cutaneous, subcutaneous and intramuscular tissue regions, especially procedures that require a precise location of a large number of sub-dermal injections.

SUMMARY OF THE DISCLOSED INVENTIONS

The disclosed inventions relate generally to automated (e.g., robotic) systems and methods for transcutaneous delivery of substances (e.g., cellular, pharmaceutical, biopolymers, peptides/proteins, small chemical molecules, etc.) into targeted cutaneous, subcutaneous and intramuscular tissue regions of a patient.

As discussed and used herein, the skin (or cutis) is considered the outer covering of a mammalian body, consisting of an outer layer (epidermis) and an inner layer (dermis). Beneath the dermis is a layer of fat ("subcutaneous fat layer"), fascia (thick connective tissue) and muscle (intramuscular regions). It will be appreciated that many substances to be delivered into the body are specifically targeted for a precise location, e.g., in or between a particular layer or layers of the skin (both epidermis and dermis). By way of non-limiting examples, stem cells for hair growth need to be injected precisely into the dermis or into the interface between the dermis and epidermis (each referred to herein as "intradermal delivery"); in a lipo-contouring procedure, fat cells need to be injected into the subcutaneous fat layer ("subcutaneous delivery"); and botulinum toxin A (Botox®) must injected directly into the muscle ("intramuscular delivery") tissue region to be effective. As used herein, the term "transcutaneous" is intended to encompass any delivery process in which the skin is pierced, including both "cutaneous" (intradermal or within the skin layers) and "subcutaneous" (beneath the skin layers) substance delivery.

In one aspect of the disclosed inventions, a method comprises maneuvering an automated arm (e.g., an image-guided robotic arm) to position a delivery device mounted on a distal end of the arm proximate a targeted location on a patient's skin surface, using a substantially automated process to (i) cause a tissue-piercing distal end of the delivery device to puncture the skin surface and penetrate a desired depth into the targeted tissue location, and (ii) deliver a controlled amount or dose of the therapeutic or cosmetic substance into the tissue.

The targeted tissue locations may include, by way of non-limiting example, areas of the scalp, face (e.g., the forehead and areas around and between eyes, nose, mouth, lips, cheeks, buttocks, calves, etc.), as well as many other body areas (especially in the case of tattoo pigment ink). The therapeutic or cosmetic substance may be in a flowable or non-flowable form. By way of non-limiting examples, the substance may comprise cells used to grow hair, e.g., hair follicular cells or inductive dermal papilla cells, pharmaceuticals that effect hair growth, such as minoxidil, finasteride, androgens/anabolic steroids, estrogen, phenytoin, retinoids, cyclosporine and other small chemical compounds under development for hair growth, as well as peptides/proteins such as Growth Hormone (GH), or a hair follicle growth factor, such as autologous platelet plasma.

By way of further, non-limiting examples, the substance may comprise non-hair related substances, such as fat cells used for lipo-contouring, clostridium botulinum toxin A (Botox®), hyaluronic acids (e.g., Restylane®), collagen-emitting fibroblasts or other forms of collagen, as well as synthetic or natural polymers that are currently available or under development for use in cosmetic or reconstructive procedures, melanocytes, calcium particles, liquid silicone, lidocane (or other anesthetics), saline solution, and tattoo pigment ink.

In embodiments in which the therapeutic or cosmetic substance is flowable, the delivery device may comprise a syringe assembly that is removably coupled to a syringe actuator carried on the automated arm. For clarity, as used herein, the term "flowable" when used to modify a substance does not mean that the substance is necessarily provided in a liquid form, or is suspended in a liquid carrier, although this may often be the case, and it will be appreciated that many solid substances are readily flowable, e.g., sand or table salt. In some embodiments, the delivery device may include a source of pressurization or a reciprocating obturator carried on the automated arm to assist in the delivery process.

The method may further include maneuvering the automated arm to reposition the delivery device proximate one or more further targeted locations on the patient's skin surface, and for each further location, using a substantially automated process to (i) cause the distal end of the delivery device to puncture the skin and penetrate a desired depth into the further targeted tissue location, and (ii) deliver a controlled amount or dose of the therapeutic or cosmetic substance into the tissue. Preferably, the automated arm may be automatically positioned at both a desired location and orientation relative to the skin surface based at least in part on images acquired of the targeted location(s), which images may include intradermal and/or subcutaneous images. In one embodiment, the automated arm is automatically positioned at the targeted location(s) based at least in part on user input, such as input relating to a desired area for facial rejuvenation or reconstruction, or relating to a desired tattoo design.

In one embodiment, an automated system for transcutaneous delivery of a therapeutic or cosmetic substance into cutaneous, subcutaneous and/or intramuscular includes an automated (e.g., robotic) arm, a delivery device carried by, and one or more cameras mounted on, the automated arm, a processor configured to receive and process images acquired by the one or more cameras, and a controller operatively associated with the processor and configured to maneuver and position the automated arm and delivery device based, at least in part, on processed images (which may include intradermal and/or subcutaneous images) acquired by the one or more cameras. The automated arm is used to position the delivery device proximate a targeted location on a patient's skin surface, wherein one or both of the processor and controller are configured to cause (i) the distal end of the delivery device to puncture the skin surface and penetrate a desired depth into the tissue at the targeted location, and (ii) a controlled delivery through the delivery device of a therapeutic or cosmetic substance into the tissue.

One or more containers or reservoirs carried on (e.g., removably coupled to) the automated arm may be used to hold the therapeutic or cosmetic substance being delivered. In one embodiment, a plurality of reservoirs are carried on the automated arm, each containing a respective therapeutic or cosmetic substance, wherein the delivery device may be selectively coupled to a respective reservoir. In one embodiment, the delivery device comprises a syringe assembly (which may be a pre-loaded) removably coupled to a syringe actuator carried on the automated arm. In other embodiments, delivery of the substance (especially if the substance is not readily flowable) may be facilitated by a source of pressurization or a reciprocating obturator carried on the automated arm.

In some embodiments, the system further comprises a user interface that allows a system operator to input instructions relating to one or more of a location, orientation and penetration depth of the delivery device. In one such embodiment, the user interface allows a system operator to input instructions relating to a type, a quantity, or both, of the therapeutic or cosmetic substance to be delivered into the targeted tissue.

In one aspect of the disclosed inventions, the automated system is used for delivery of a therapeutic or cosmetic substance into or proximate cutaneous and/or subcutaneous tissue at least partially surrounding or otherwise proximate to one or more existing hair follicles in a body surface of a patient. In one such embodiment, a method for delivering a therapeutic or cosmetic substance proximate cutaneous and/or subcutaneous tissue of one or more existing hair follicles includes maneuvering an automated arm (e.g., an image-guided robotic arm) to position a delivery device mounted on the automated arm proximate an existing (e.g., "miniaturized") hair follicle, and then using a substantially automated process to (i) cause a tissue-piercing distal end of the delivery device to puncture the skin surface and penetrate a desired depth into the cutaneous and/or subcutaneous tissue at least partially surrounding, or otherwise proximate to, the targeted hair follicle, and (ii) deliver a therapeutic or cosmetic substance therein.

As noted above, the therapeutic or cosmetic substance may be (although it is not a requirement) in a readily flowable form, and may be supplied from one or more containers or reservoirs carried on (e.g., removably coupled to) the automated arm. By way of non-limiting examples, the therapeutic or cosmetic substance may comprise substances such as stem cells, hair inductive dermal papilla cells; pharmaceuticals that effect hair growth, such as minoxidil, finasteride, androgens/anabolic steroids, estrogen, phenytoin, retinoids, cyclosporine and other small chemical compounds under development for hair growth; and peptides/proteins such as Growth Hormone (GH), or a hair follicle growth factor, such as autologous platelet plasma.

The method of this embodiment may include maneuvering the automated arm to reposition the delivery device proximate one or more further existing hair follicles, and for each additional hair follicle, using a substantially automated process to (ii) cause a tissue-piercing distal end of the delivery device to puncture the skin surface and penetrate a desired depth into the cutaneous and/or subcutaneous tissue at least partially surrounding, or otherwise proximate to, the respective targeted hair follicle, and (ii) deliver a therapeutic or cosmetic substance therein.

The automated arm may be automatically positioned at the targeted hair follicle(s) based at least in part on images (including intradermal and/or subcutaneous images) acquired of the skin surface. The delivery device may be positioned at a desired orientation relative to a targeted hair follicle prior to puncturing and penetrating the skin surface. In some embodiments, the distal end of delivery device at least partially surrounds the respective targeted hair follicle as it penetrates the skin surface. In other embodiments, the delivery device axis forms an angle with the targeted hair follicle as the delivery device punctures and penetrates the skin surface. In some embodiments, the therapeutic or cosmetic substance is delivered at multiple discrete locations in the cutaneous and/or subcutaneous tissue proximate to the targeted hair follicle(s).

In some embodiments, the automated system comprises a user interface that allows a system operator to input instructions relating, by way of non-limiting example, to at least one of a location, orientation and penetration depth of the distal end of the delivery device relative to the targeted hair follicle(s). In some such embodiments, the user interface allows a system operator to input instructions relating to a type, a quantity, or both, of the therapeutic or cosmetic substance to be delivered.

Other and further embodiments and aspects of the disclosed inventions will become apparent from the attached drawings, when viewed in conjunction with the following, detailed description thereof.

BRIEF DESCRIPTION OF THE DRAWINGS

Embodiments of the present inventions are illustrated by way of example and not limitation in the figures of the accompanying drawings, in which like reference numbers indicate similar elements, and in which:

FIGS. 7A-D are simplified, partially cut-away views of a procedure in which a flowable substance is delivered from a delivery cannula into a targeted subcutaneous and cutaneous body tissue regions.

FIGS. 8A-D are simplified, partially cut-away views of a procedure in which solid or semi-solid cellular material pellets are delivered from the delivery cannula into a targeted subcutaneous body tissue region.

FIGS. 9A-D are simplified, partially cut-away views of a procedure in which a delivery device cannulates an existing hair follicle and delivers a flowable substance to subcutaneous and cutaneous tissue substantially surrounding the follicle.

FIGS. 10A-D are simplified, partially cut-away views of a procedure in which a delivery device cannulates an existing hair follicle and delivers solid or semi-solid cellular material pellets to subcutaneous tissue proximate to the follicle.

DETAILED DESCRIPTION OF THE ILLUSTRATED EMBODIMENTS

Figure 1:
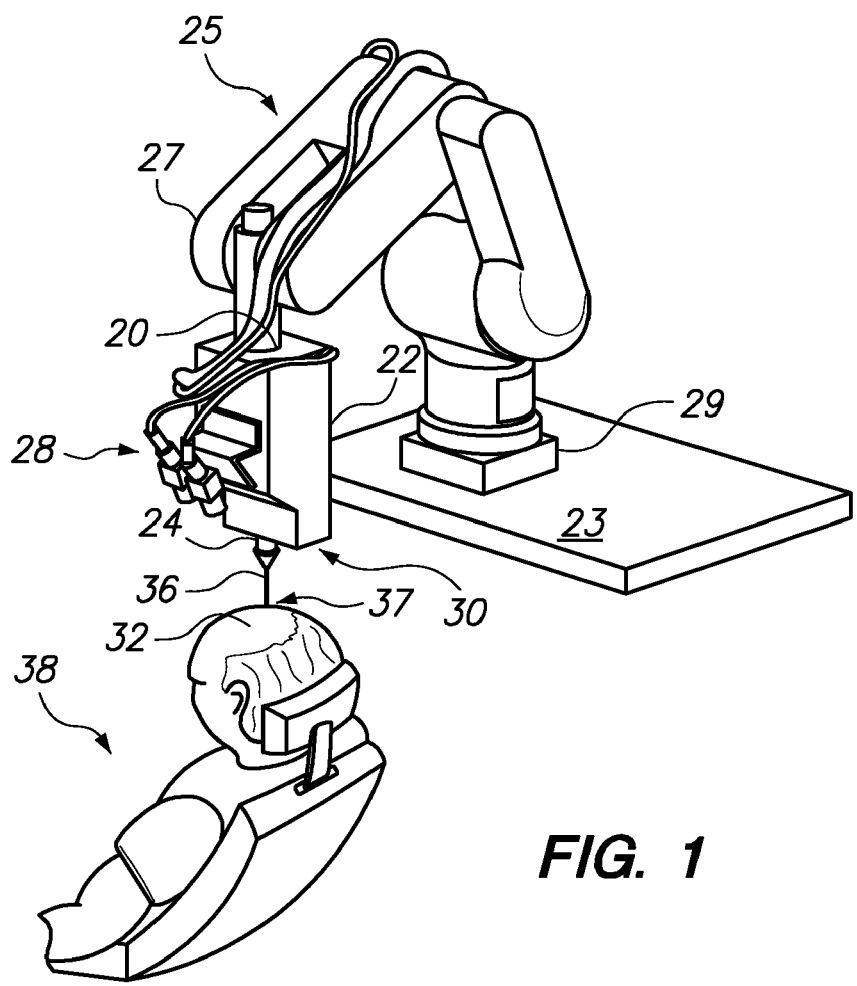
FIG. 1 is a perspective view of a robotic arm system used for positioning and orienting a transcutaneous delivery cannula extending from an delivery device actuator housing mounted on a distal end of the robotic arm.

Automated systems and apparatus constructed and operated according to various embodiments of the invention may be used to deliver (e.g., deposit or inject) various therapeutic and cosmetic substances to targeted cutaneous, subcutaneous and/or intramuscular tissue regions of a mammalian body. It will be appreciated that a substance being delivered may be selected for cosmetic reasons, (whether aesthetic, reconstructive, or both), for therapeutic reasons (whether curative or palliative), or for a combination of cosmetic and therapeutic reasons. A number of substances are particularly well-suited for delivery using an automated system of the invention, especially substances that are currently or proposed to be delivered in procedures requiring a number of precise, small quantity, transcutaneous injections into cutaneous, subcutaneous or intramuscular tissue regions using a hand-held syringe.

By way of non-limiting examples, the delivered substances may include cells obtained from both autologous and allogeneic sources, such as stem cells used to grow hair e.g., hair follicular cells or inductive dermal papilla (or sheath) cells, a hair follicle growth factor (e.g., an autologous platelet plasma), or fat cells used for facial or body lipo-contouring. Many non-cellular substances may also be advantageously delivered to cutaneous, subcutaneous and intramuscular tissue regions using an automated system, such as pharmacologic products, e.g., finasteride (Propecia®) and minoxidil (Rogaine®), delivered directly into or proximate the cutaneous and/or subcutaneous tissue of miniaturized, dormant and normal hair follicles.

By way of further example, non-hair transplantation related sub-dermal implants and treatments such as intradermal fibroblasts and collagen, intramuscular clostridium botulinum (Botox®), and intradermal and subdermal synthetic and natural polymers. Hyaluronic acid-based products (e.g., Restylane®) for facial and other body area restoration and rejuvenation may also be intradermally or subcutaneously delivered to tissue regions using an automated system of various embodiments of the invention. By way of yet another example, in one embodiment, an automated system is used for intradermal delivery of pigments for generating face and other body surface tattoos.

Other substances, such as small chemicals, biologics, and peptides, as well as others mentioned in the "Summary of Disclosed Inventions" section of the specification, may also be suitable for delivery using an automated system of various embodiments of the invention. Some more specific information about many of the substances that may be delivered using embodiments of the invention follows. This information is intended to be illustrative, and not limiting, and it will be appreciated by those skilled in the art that embodiments of the invention may deliver other substances to targeted cutaneous, subcutaneous and intramuscular tissue regions.

Cells for Inducing or Facilitating Hair Growth

Autologous hair regeneration therapy has been developed for the treatment of both male and female pattern baldness, as well as female diffuse alopecia. In accordance with this process, a small sample of hair follicles is taken from the patient during a relatively simple operation carried out under local anesthetic, e.g., at a hair or skin clinic. The hair-inductive dermal papilla cells from the sample are dissociated from the rest of the follicle, cultured and expanded in proprietary media, and subsequently returned to the clinic in a sterile suspension media, where the hair-inductive dermal papilla cells are intradermally delivered into the patient's scalp. The treatment may be performed under local anesthetic and comprises a single procedure of a number of superficial injections, each injection delivering a minute volume of media containing dermal papilla cells capable of inducing new hair growth.

More particularly, it has been shown that hair follicle inductive cells, such as inductive dermal papilla (or sheath) cells, may be implanted in a reproducible manner, in which controlled amounts of the cells are delivered at an appropriate depth from the surface of the epidermis, typically into the dermis between the dermis and epidermis. The inductive dermal papilla (or sheath) cells may be derived from a variety of sources, such as mesenchymal stem cells, mesodermal progenitor cells, and hematopoietic stem cells derived from harvested bone marrow taken from the patient. For example, PCT Publication W001/11011 describes multi-potent adult progenitor cells, and is hereby incorporated by reference in its entirety. Another source of cells is pluri-potent cells derived from the patient's skin. See, e.g., Toma, J. G. et al., Nature Cell Biol. 3: 778-784 (2001), which is hereby incorporated by reference in its entirety.

Alternatively, the inductive dermal sheath and/or inductive dermal papilla cells may be derived from embryonic stem cells or embryonic carcinoma cells that have been suitably differentiated toward a DP phenotype for hair using known methods. For example, teratomas, from which embryonic carcinoma cell lines can be derived, have hair and teeth-like structures. Such embryonic carcinoma cells are commercially available from Layton Biosciences, for example. Allogeneic sources of stem cells allow for standardization, (potentially) better quality control on stem cell production, elimination of the harvesting part of the procedure, and immediate access to a large amount of donor cells. It also opens up the possibility of having the patient choose to change their hair type. For example, a patient with straight hair can elect to have stem cells that produce curly or wavy hair implanted into their scalp. Other characteristics can be selected as well, e.g., hair color, hair caliber, etc. A further source of cells is reprogrammed cells, for example, autologous cells, that have been "reprogrammed" by dermal papilla cells or embryonic carcinoma cells to induce hair formation. For an understanding a reprogramming of autologous cells, see PCT Publication WO00/49138, which is hereby incorporated by reference in its entirety. Cells having a desired functionality of hair inductiveness may be stably maintained in culture using known methods. See, for example, U.S. Pat. No. 5,851,831, which describes a long term subculture of dermal papilla cells, as well as the methods disclosed in PCT Publication No. WO01/74164, which are each hereby incorporated by reference in their entirety.

When they are ready for implantation in the patient, the inductive dermal sheath cells and/or inductive dermal papilla cells are delivered to a depth from an outer skin surface where normal hair follicles form in vitro (e.g. in cultured skin) or in vivo (i.e. in a person or other mammal). Delivery of the inductive cells to the correct depth allows inducted hair follicles to be embedded in the dermis so that developed hairs will be better anchored and less susceptible to mechanical stresses such as pulling, combing or brushing. For example, the desired depth may range from the dermis to the subcutaneous fat (located at a depth of approximately 0.5-10 mm). A controlled delivery device provided by embodiments of the invention advantageously allows the depth and dosing amount of each delivery to be precisely determined and consistently reproduced, while being adjustable for particular delivery situations.

The inductive dermal sheath cells and/or inductive dermal papilla cells may be delivered at a given angle (orientation) within or between the dermal layers. In one embodiment, the controlled delivery device first generates an implantation track using cannula with a blunt end and an orifice on a lateral side near the tip (for example, an orifice approximately 0.5 mm from the tip), allowing cells to be implanted along the needle track. The controlled delivery device may dispense in suspension between 1000 and 40000 inductive dermal sheath cells and/or inductive dermal papilla cells per delivery. The controlled delivery device may dispense inductive dermal sheath cells and/or inductive dermal papilla cells in suspension at a cell density of between 500,000) and 4,000,000 cells/ml per delivery dose.

The controlled delivery device may alternatively dispense preformed aggregates or clumps (e.g., formed into soft pellets) of inductive dermal sheath cells and/or inductive dermal papilla cells. For example, each pre-formed aggregate may contain between 1500 and 10,000 cells, with one to three pre-formed aggregates dispensed per delivery location. Cells or aggregates of cells may be placed in a formulation, such as hyaluronic acid or glycosaminoglycans, that includes a substance (or substances), which increases the viscosity of the injected material in order to protect the cells during handling and injection.

Cells or aggregates of cells may also be placed in a formulation, for example, one including fibrin, fibronectin and/or collagen or other extra-cellular matrix molecules known to those skilled in the art for enhancing the microenvironment of the cells after implantation, in order to facilitate cell migration and/or cell-cell interaction. Delivery of the inductive cells to the correct depth allows induced hair follicles to be imbedded in the dermis, so that developed hairs will be better anchored and less susceptible to being pulled out when placed under mechanical stress such as combing or brushing. Also, culturing the cells with a keratinocyte conditioned medium may increase successful retention of the implanted "new" hair follicles.

Growth Factors for Existing Hair Follicles

According to another embodiment, growth factor is delivered to a patient with the automated delivery system described herein. It is known, for example, that the formation or regeneration of a senescent hair follicle can be induced by contacting the epidermal tissue with certain growth factors in the absence of added papilla cells, as disclosed in U.S. Patent Application Publication No. 2003/0198646 ("Stenn"). In particular, Stenn discloses inserting a removable, biologically inert vehicle capable of contacting the epidermal layer in the skin. It further discloses inserting the vehicle into epithelial layer in an orientation found to be cosmetically acceptable, secured to the skin, and left in the insertion site to facilitate the formation of an epithelial cell column that will eventually form the hair follicle. According to Stenn, the vehicle may be treated or coated with a growth factor or a transcription factor, or a construct expressing these factors, to facilitate to facilitate hair follicle formation and hair growth and the vehicle is removed from the epidermal layer after a prescribed period of time.

In accordance with another embodiment, it has been observed that using autologous platelet plasma as a growth factor for temporarily storing harvested hair follicular units prior to when they are implanted may improve hair transplantation yield by 15%. In particular, a hair transplantation patient's blood is used to generate (with centrifuge) the platelet growth-factor-rich plasma, in which the patient's harvested hair follicular units are kept instead of a (typical) saline solution. Thus, it may be advantageous to use an automated system of the present invention to deliver a growth factor substance, such as autologous platelet plasma, to the cutaneous and/or subcutaneous tissue of, or proximate to, existing or newly transplanted hair follicles or hair follicular units.

Small Molecules

Small chemical molecules may be delivered to a desired depth in the cutaneous, subcutaneous or intramuscular tissue. One example is finasteride, commercially available under the trade name Propecia® (www.propecia.com), a synthetic androgen inhibitor used primarily in men for the treatment of benign prostatic hyperplasia and androgenetic alopecia. Finasteride appears to significantly reduce the formation of DHT, is a substance in the body that can shrink the hair follicle until it no longer produces visible hair. In one embodiment, small aliquots of finasteride are injected intradermally into the tissue comprising or in the proximity of effected hair follicles. Another example is minoxidil, commercially available under the trade name of Rogaine® (www.rogaine.com), which has been shown to stimulate hair growth on the bald spot of the back of the head in men, and to increase hair growth in the forehead areas of women when topically delivered. It is believed that intradermal injections of minoxidil will also be effective to stimulate and/or increase hair growth.

So-called "hedgehog" small molecule agonists can be used to stimulate or inhibit the growth of hair via hedgehog signaling pathways, as described in U.S. Pat. No. 6,639,051, which is incorporated herein by reference in its entirety. Briefly, the body's regulatory signaling pathways are the means by which tissues and organs exchange instructional messages that regulate specific biological functions. Hedgehog signaling pathways act by initiating cascades of other pathways required for tissue formation and regulation. These pathways appear to control the expression of tissue growth factors and blood vessel growth factors, for example, to repair damage and regenerate tissues. Small molecule hedgehog pathway inhibitors and hedgehog blocking antibodies have been developed by Curis, Inc. (www.curis.com), including a small molecule agonist of the hedgehog signaling pathway that can stimulate the transition of hair follicles from the resting to the growth stage of the hair cycle to treat both male and female pattern baldness. It is believed that intradermal injections of such hedgehog small molecule agonists will be effective to stimulate and/or increase hair growth.

Factors that Affect Hair Follicle Cycling

Each hair follicle perpetually goes through three stages: growth (anagen), involution (catagen), and rest (telogen). Activation and deactivation of molecular signals orchestrate the follicle's transit between these stages. There are many substances that modulate hair growth in humans. Each substance has been documented to have a predictable effect on hair. By way of non-limiting examples: Androgen, a steroid hormone (such as testosterone or androsterone) which controls development and maintenance of masculine characteristics, promotes miniaturization of follicles and shortens the duration of the anagen stage in androgen-sensitive areas of the scalp. Androgen also enlarges follicles in androgen-dependent areas (e.g., male beard). Estrogen (a steroid hormone associated with the development and maintenance of female sex characteristics) prolongs the anagen growth stage. Anabolic steroids have the same actions as androgens.

Retinoids (any of various natural or synthetic derivative of vitamin A) can cause premature onset of the catagen stage. Cyclosporin (a substance, synthesized by certain soil fungi, that suppresses the immune response by disabling help T cells, used commonly to minimize rejection of foreign tissue transplants) can cause hypertrichosis, i.e., excessive growth of hair (e.g., hirsutism). Phenytoin (available under the trade name Dilantin®), a commonly used anti-convulsant medicine to treat seizures, may also cause hypertrichosis. Such pharmaceutically active substances may be injected intradermally to affect the activity of the hair follicles and skin. Further information relating to the forgoing substances may be found in, "The Biology of Hair Follicles," by Paus & Cotsarelis, New England Journal of Medicine (1991), 341(7), pp 491-497, which is also the source of the information set forth in the preceding two paragraphs.

Facial and Other Body Implants and Substances; Lipo-Contouring

Proteins, peptides, antibodies or toxins may be delivered to a desired site with one of the automatic delivery systems described herein. In one example, Botox® (available from Allergan), the brand name of a toxin produced by the bacterium clostridium botulinum. In large amounts, this toxin can cause botulism, but it has also been used as an injectable muscle relaxant for smoothing wrinkles (including when implanted in combination with various wrinkle fillers), e.g., around the eyes and forehead. Small, diluted amounts can be directly injected into specific muscular tissues causing controlled weakening of the muscles. The FDA approved such usage in the late 1980s upon the discovery that Botox® could stop ailments like blepharospasm (uncontrolled or spasmodic blinking/winking) and strabismus (lazy eye). Cosmetic physicians have been using Botox® for years to successfully treat wrinkles and facial creases. In April 2002, Botox® gained FDA approval for treatment of moderate-to-severe frown lines between the eyebrows—called glabellar lines. However, Botox® is often used for other areas of the face as well. Similar substances include Reloxin (available in the U.S. from Medicia Corporation; sold in Europe under the name Dyspot) and Puretox (available from Mentor Corporation).

According to yet further embodiments, biopolymers and synthetic polymers may be intradermally or subdermally delivered in one or more sites along a patient's skin surface using an automated delivery system described herein. One example is Restylane® (supplied by Q-Med AB; www.restylane.com), a cosmetic dermal filler made from non-animal stabilized hyaluronic acid, and may be intradermally or subdermally implanted to restore volume and fullness to skin, e.g., for reducing or eliminating facial wrinkles and folds, such as (but not limited to) nasolabial folds. In particular, hyaluronic acid is a substance found naturally in the human body, which is hydrophilic (or "water loving"). As hyaluronic acid gradually degrades, each molecule binds to more water and over time, the same special volume can be maintained with less hyaluronic acid.

Other hyaluronic acid-based products include Perlane (from Medicis—awaiting FDA approval as of the filing date of this patent), Juvederm (from Allergan to compete with Restylane and may be easier to inject); older and possibly less desirable products from Allergan include Haylaform and Captique; Puragen Plaus (from Mentor corp.), a hyaluronic filler expected to last about 6 months, and includes lidocane anesthetic. Examples of biomaterials include Laress (FziOMed, Inc., San Luis Obispo, Calif.) used in spine surgery and under development for use as a filler, and Aquamid (Contura Intl, Denmark), a permanent filler made from a biomaterial used in contact lenses and other medical devices.

So-called "fibroblasts" maybe delivered both intradermally and subdermally for facial rejuvenation. Allogeneic, collagen-secreting human dermal fibroblasts (HDFs) are believed to have the ability to enhance the skin's collagen support matrix, thus enabling the appearance of facial wrinkles and folds to be improved, e.g. glabellar lines (between the eyebrows), perioral lines (around the mouth), and periorbital lines (around the eye). The aim is to provide a more youthful appearance, helping to combat the cosmetic effects of aging. A minute volume of cells are injected into the affected tissue regions (e.g., in the lips) using local anesthesia. The benefit is expected to become apparent once injected HDFs have begun to lay down new collagen within the dermis. This effect is expected to be sustained, providing long-term enhancement of the facial appearance. It is anticipated that repeat administrations will be given as required.

Collagen products include CosmoDerm™ and CosmoPlast (Allergan), which are made in a laboratory from human collagen, which is a natural component of the skin, and are used for treatments of deeper lines and furrows, and is also popular in the lip border and fine lines above the mouth. Another collagen product is Evolence™, being developed by Cobar Sciences (Johnson & Johnson). Zyderm® and Zypoplast® (both from Allergan) are made from refined bovine dermal collagen. Synthetic polymers used as implants include Sculptera™ (Dermik Laboratories, a division of Sanofi Aventis) is a synthetic polymer approved for treating facial fat loss in HIV patients. Radiesse™ (BioForm Medical, San Mateo, Calif.) is an implant made from tiny calcium particles that create a scaffold for the body's own collagen to grow. Radiesse is approved in the US for cranial facial surgery and awaiting approval for smile line wrinkles. Liquid Silicone (Alcon Inc.) is a purified product for eye surgery and an option for filing facial scars. ArteFill™ (Artes Medical) is a permanent implant used to treat smile lines and acne scars.

In a "lipo-contouring" procedure, fat cells are harvested from the body (e.g. abdomen, thighs, buttocks, etc.), typically in a liposuction process. These fat cells are then processed and, with an automated system according to the invention, may be injected into areas of the face and body where rejuvenation and reconstruction are needed. The fat cells can be used as "fillers" in the face to eliminate or lessen the appearance of wrinkles. They also can be used as filler in the lips. Injected fat cells can also be used to augment the natural soft tissue pads of the face and body that have atrophied with age, e.g. cheeks, forehead, hands, etc.

Injection/Delivery of Pigments (Tattoo Application)

A tattoo is a permanent mark or design made on the body when pigment is inserted into the dermal layer of the skin through ruptures in the skin's top layer. When you observe person's tattoo, you are observing the ink through the epidermis, or the outer layer of skin. The ink is actually implanted/injected in the dermis (underlying) skin layer, since the cells of the dermis are far more stable than the cells of the epidermis, resulting in tattoo ink staying in place, with minor fading and dispersion, for a person's entire life.

Modern-day tattoos are applied by using an electric tattoo machine, with needles that rapidly puncture the skin with an up and down motion not unlike that of a sewing machine. To do this, an electrically powered tattoo machine that resembles (and sounds like) a dental drill is typically used. The machine is hand-held, and moves a solid needle up and down to puncture the skin between 50 and 3,000 times per minute. The needle penetrates the skin by about a millimeter and deposits a drop of insoluble ink into the skin with each puncture. Punctures that are too deep can cause excessive pain and bleeding, and ones that are too shallow cause uneven lines. Embodiments of the automated system and methods provided by the present inventions include ones that are customized for autonomous or substantially autonomous intradermal delivery of tattoo pigment ink to precise and consistent depths and locations in the dermis.

Other Substances and Applications

A substance such as a saline solution can be delivered by an automated system provided by embodiments of the invention to create tumescence (expanded tissue) in a region, which can be a desired state for an ensuing surgical procedure, such as hair transplantation, where tensioning of the scalp can enhance needle delivery through the skin. An anesthetic, such as a lidocane solution, can also be delivered to the pertinent cutaneous, subcutaneous or intramuscular tissue regions using an automated system provided by embodiments of the invention, again, in advance of a further procedure. Melanocytes are cells located in the bottom layer of the epidermis and affect a person's natural skin pigmentation, or color. There are typically between 1000 and 2000 melanocytes, per square millimeter of skin, i.e., comprising 5% to 10% of the cells in the basal layer of epidermis. The difference in skin color between fair-skinned people and dark-skinned people is not due to the number of melanocyte cells in their skin, but instead is due to the level of activity of the melanocyte cells. Further information regarding melancytes may be found at http://en.wikipedia.org/wiki/Melanocytes. Melancytes can also be delivered (whether for therapeutic or cosmetic purposes) to targeted cutaneous tissue regions using an automated system provided by embodiments of the invention.

Automated Delivery Systems and Methods of their Use

FIG. 1 depicts an image-guided robotics system 25, including a robotic arm 27 with a delivery tool assembly 30 attached to a distal tool plate 20 of the robotic arm 27. The delivery tool assembly 30 includes a delivery needle (or "cannula") 36 extending from a tubular body 24, which in turn extends from a delivery tool housing 22 attached to the tool plate 20. The delivery cannula 36 is axially stiff, e.g., made of a hard metal or plastic, and thin-walled to facilitate tissue penetration, and has a beveled, tissue piecing, open distal tip.

The robotic arm 27 has a base 29 mounted on a stable platform (table) 23. A patient 38 is positioned relative to the robotic arm 27, so that a targeted body surface (in this instance, the patient's scalp) 32 is directly underlying the distal tip 37 of the delivery cannula 36. The actual dimensions of the cannula 36 (e.g., its respective inner and out diameters) may vary in accordance with embodiments of the invention, depending, for example, on the particular therapeutic or cosmetic procedure to be performed and/or the particular substances to be delivered into (or otherwise through) the targeted tissue region(s). As is taught in the above-incorporated U.S. patent application Ser. Nos. 11/380,903 and 11/421,438, the robotic system 25 includes one or more cameras 28 (two are visible in FIG. 1) mounted on the delivery tool housing 22 (which in turn is mounted on the distal end tool plate 20 of the robotic arm 27). A processor (not shown) associated with the robotic system 25 receives and processes images acquired by the one or more cameras. The robotic system 25 includes a controller (also not shown) that is operatively associated with the processor and configured to precisely maneuver the arm 27 in six degrees of freedom based, at least in part, on images acquired by the one or more cameras 28 and processed by the processor. The images may include both intradermal and subcutaneous images.

In particular, the robotic arm 27 is maneuverable so that the delivery cannula 36 may be positioned proximate a targeted location on a patient's skin surface, wherein (as described in greater detail herein) one or both of the processor and controller are configured to cause (i) a distal end 37 of the delivery cannula 36 to puncture the skin surface and penetrate into tissue at the targeted location, and (ii) a controlled delivery through the delivery cannula 36 of a therapeutic or cosmetic substance into the tissue. As is taught in the above-incorporated U.S. patent application Ser. Nos. 11/380,903 and 11/421,438, the robotic system 25 preferably includes a user interface (not shown) that allows a system operator to input instructions relating to one or more of a location, an orientation and a penetration depth of the delivery cannula 36. Such a user interface additionally or alternatively preferably allows a system operator to input instructions relating to a type, a quantity, or both, of the therapeutic or cosmetic substance to be delivered into a targeted tissue region.

Various embodiments of the robotic system 25 may be configured for delivery of therapeutic and cosmetic substances, including but not limited to all of the above-mentioned therapeutic and cosmetic substances, into target cutaneous, subcutaneous and intramuscular tissue regions. Towards this end, under image guidance and verification, at a desired location, embodiments of the robotic system 25 precisely (and repeatedly) position the tissue piercing distal tip 37 of the delivery cannula 36 at respective desired (i.e., "targeted") locations at, and in desired orientation(s) relative to, a patient's skin surface. By way of illustration and not limitation, a desired orientation may include a particular angle of approach of the delivery cannula 36 relative to the patient's skin surface, or a relative orientation of the beveled, open distal tip 37 of the delivery cannula 36 as it punctures and penetrates the skin surface, e.g., with the tip opening facing into, or away from, the skin surface.

A number of differing delivery tool assemblies 30 may be housed in the delivery tool housing 22, with each delivery tool assembly 30 configured for operating in conjunction with, and under the common control of, the robotic system 25. Relative motion of the delivery cannula 36 for causing the tissue-piercing distal tip 37 to puncture and penetrate the skin surface to a desired penetration depth into the cutaneous, subcutaneous or intramuscular tissue may be provided by movement of the robotic arm relative to the skin surface. Additionally or alternatively, relative motion of the delivery cannula 36 to the skin surface may be provided by embodiments of the deliver tool assembly 30. Regardless of how such relative motion of the delivery cannula 36 is accomplished, the respective delivery tool assemblies are configured to deliver precisely metered doses or amounts of both flowable and non-flowable therapeutic and cosmetic substances into the targeted cutaneous, subcutaneous and intramuscular tissue regions.

Figure 6A:
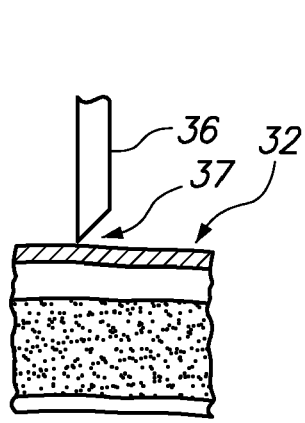
FIGS. 6A-B are simplified, partially cut-away views of a procedure in which a flowable substance is delivered topically from a delivery cannula onto a skin surface of a patient.
Figure 6B:
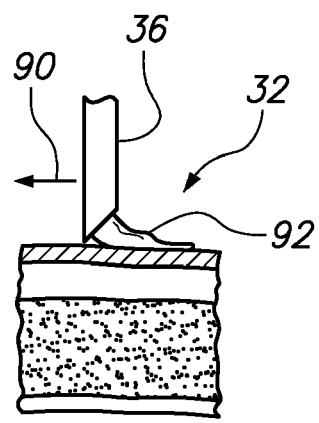

As illustrated in FIGS. 7-9, various embodiments of the system 25 and delivery tool assemblies 30 may provide for the therapeutic or cosmetic substance to be delivered at multiple discrete locations in a single tissue penetration track made by the delivery cannula 36. By way of example, a substance (whether flowable or non-flowable, e.g., soft cellular matter pellets) may be metered out at a constant flow/dispensing rate as the as the delivery cannula 36 is retracted out of a tissue track formed by a single penetration movement of the delivery cannula 36, from a location of its deepest penetration (e.g., in a subcutaneous fat layer) to a location closer to the skin surface (e.g., in between the dermis and the epidermis). In addition to transcutaneous delivery, various embodiments of the robotic system 25 may be used for topical (skin surface) substance delivery, as illustrated in FIGS. 6A-6B (depicting the release of a flowable substance 92 from the open distal end 37 of the delivery cannula 36 onto a targeted region of a patient's skin surface 32, as the cannula 36 is moved laterally along the skin surface 32, indicated by arrow 90).

Various illustrated embodiments of the delivery tool assemblies 30, as well as illustrations of the delivery of therapeutic or cosmetic substances using such embodiments, will now be described. It will be appreciated that other and further embodiments are possible, as well as modifications to the illustrated and described embodiments. It will be further appreciated that various features and parts of the individual embodiments may be interchangeable and used on other embodiments, even if not so-illustrated. Thus, the illustrated and described embodiments are for purposes of better understanding, and not limitation, of the inventions disclosed herein.

Figure 2A:
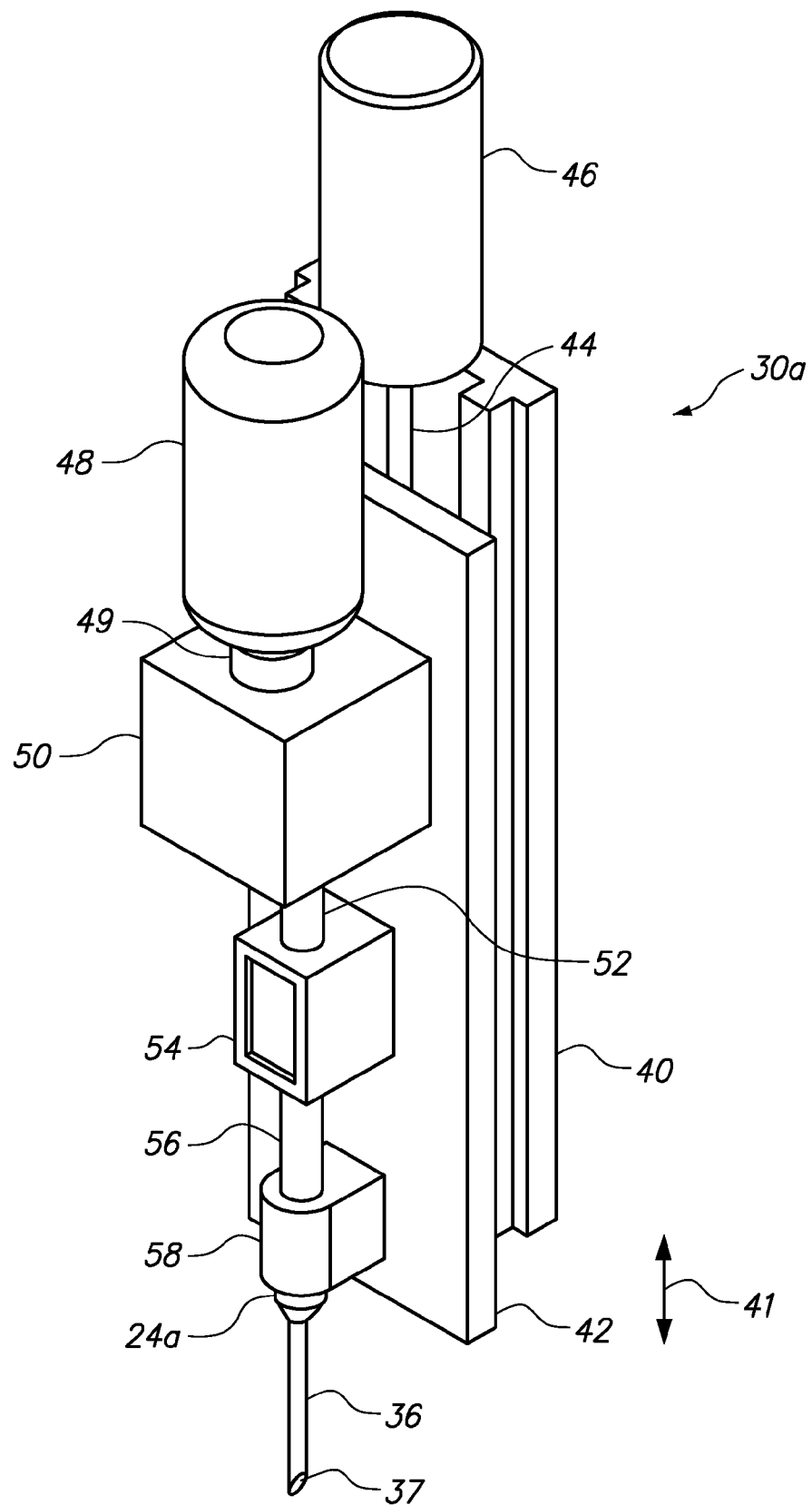
FIG. 2A is a partially schematic, perspective view of one embodiment of a delivery device carried in the actuator housing of the system of FIG. 1, and configured for transcutaneous delivery of a flowable therapeutic or cosmetic substance into body tissue.

FIG. 2A is a partially schematic, perspective view of one embodiment of the delivery tool assembly 30 (designated 30A) for use in the robotic system 25. The delivery tool assembly 30A includes an anchor plate 40 that is fixed (not shown) to an inner wall of the delivery tool housing 22, and a delivery tool plate 42 that is movably coupled to the anchor plate 40. In particular, the delivery tool plate 42 is movable along a screw or similar longitudinal tack 44 relative to the anchor plate 40 by a motor 46, in a well known manner. The delivery cannula 36 is fixed to the delivery tool plate 42 by one or more guides 58 (a single guide 58 is shown in FIG. 2A), whereby the delivery cannula 36 may be advanced out of, or retracted into, the delivery tool housing 22 by movement the delivery tool plate 42 relative to the anchor plate 44, as indicated by the two-way arrows 41. The delivery tool assembly 30A further includes a reservoir 48 for holding a supply of a flowable therapeutic or cosmetic substance to be controllably delivered through the distal end 37 of the delivery cannula 36 at target tissue locations.

In particular the reservoir 48 is fluidly coupled to an inlet 49 of a pump 50, which is preferably fixed to the delivery tool plate 42 for stability. The reservoir 48 is preferably readily detachable from the pump inlet 49 for easy refill or replacement. An outlet 52 of the pump 50 passes through a flow meter 54. A processor (not shown) associated with the robotic system 25 (which is preferably although not necessarily the same processor that controls movement of the robotic arm 27), controls operation of the pump 50 based on input from the flow meter 54 and other input parameters, in order to precisely dispense metered doses of the therapeutic or cosmetic substance from the reservoir 48, through an outlet line 56, tapered portion 24a, and the delivery cannula 36, respectively, to a targeted tissue location at or in which the distal opening 37 of the cannula 36 is positioned. Other input parameters taken into account by the processor for controlling operation of the pump 50 and, thus, output of the flowable substance through the cannula 36, may be supplied from a stored-program and/or a user-interface, and may be related, for example, to one or more of a type of procedure being performed, a type of substance being delivered, a location in which the substance is being delivered.

During a procedure performed using the system 25 with the delivery tool assembly 30A to deliver (i.e., inject) precise doses of a therapeutic or cosmetic substance carried in the reservoir 48 to specific targeted cutaneous, subcutaneous or intramuscular tissue regions in a patient, a system operator, an automated program, or a combination of each, directs the controller to maneuver the robotic arm 27 until the delivery cannula 36 is at a desired position and orientation proximate a targeted location on a patient's skin surface. Such movement is normally controlled, at least in part, through image-guidance based on images obtained from the one or more cameras 28 (as taught in the above-incorporated U.S. patent application Ser. Nos. 11/380,903 and 11/421,438).

Once the delivery cannula 36 is in a desired position/orientation relative to the patient's skin surface, a system processor causes the motor 46 to move the delivery tool plate 42 relative to the anchor plate 40, to thereby cause the tissue-piercing distal end 37 of the cannula 36 to puncture the skin surface and penetrate a desired depth into the tissue at the targeted location. Alternatively or additionally, movement of the delivery cannula 36 relative to the patient's skin surface can be accomplished by further movement of the robotic arm 27 relative to the patient's skin surface. As discussed above, the penetration depth of the tip 37 of the delivery cannula 36 (and, thus, the degree of movement by the motor 46 of the delivery tool plate 42 relative to the anchor plate 40) will depend on which tissue region(s) (i.e., epidermis, dermis, subcutaneous fat layer, intramuscular tissue region) the substance is to be injected into. The actual depth of the respective tissue region boundaries may vary from patient to patient, and a particular desired penetration depth for given patient may be dependent on intradermal and subcutaneous images acquired by the one or more cameras 28 (or otherwise acquired by a different tissue imaging modality), from which the tissue layer depths may be determined.

Once the cannula tip 37 is positioned at a desired depth, the system processor activates the pump 50 to thereby dispense a desired quantity of the flowable therapeutic or cosmetic substance into the tissue region. By way of illustration, with reference to FIGS. 7A-7D, by image-guided maneuvering of the robotic arm 27, the tissue-piercing distal tip 37 of the delivery cannula 36 is positioned (and oriented) at targeted location 31 on a patient's skin surface 32 (shown in FIG. 7A). Thereafter, as indicated by arrow 94 in FIG. 7B, the delivery cannula 36 punctures and penetrates into the skin surface 32, through the epidermis 100 and dermis 102, until the cannula distal tip 37 reaches a desired depth of penetration in the subcutaneous fat layer 104. Thereafter, as shown in FIG. 7C, a metered dose of a therapeutic or cosmetic substance 95 is released through the delivery cannula 36 into the subcutaneous tissue 104. In the illustrated example, the substance 95 continues to be released from the cannula 36 into the tissue as the cannula 36 is withdrawn from the subcutaneous fat layer 104 and back through the dermis 102, as indicated by arrow 96 in FIG. 7D.

Figure 2B:
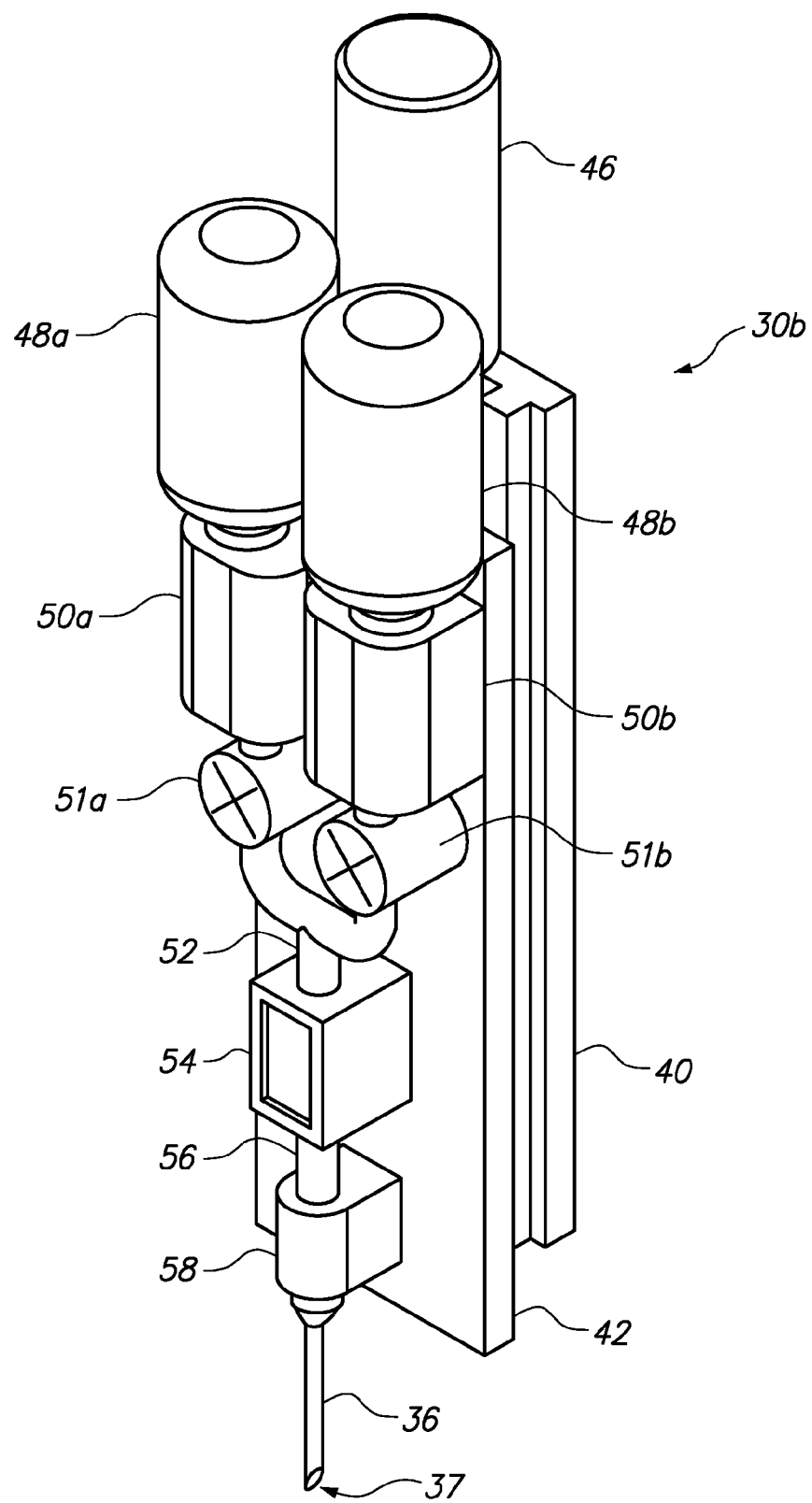
FIG. 2B is a partially schematic, perspective view of an alternate embodiment of the delivery device of FIG. 2A.

FIG. 2B is a partially schematic, perspective view of an alternate embodiment of the delivery tool assembly 30A (designated 30A'), which may be mounted in the delivery tool housing 22. The delivery tool assembly 30A' is substantially identical to the delivery tool assembly 30A, except that two separate reservoirs 48A and 48B are provided, which may be used for storing alternative therapeutic or cosmetic substances to be delivered through the delivery cannula 36. In particular, the reservoirs 48A and 48B are fluidly coupled to respective (separately controllable) pumps 50A and 50B. The outlets of pumps 50A and 50B are, in turn, fluidly coupled to (separately controllable) valves 51A and 51B, which have outlets joined into a single fluid inlet 51 of the flow meter 54. In this manner, the system processor my selectively open a valve 51A or 51B, in conjunction with activating a respective pump 50A or 50B, in order to dispense a desired quantity of a flowable therapeutic or cosmetic substance in a respective one of the reservoirs 48A or 48B through the delivery cannula 36 and into a targeted tissue region.

Figure 3:
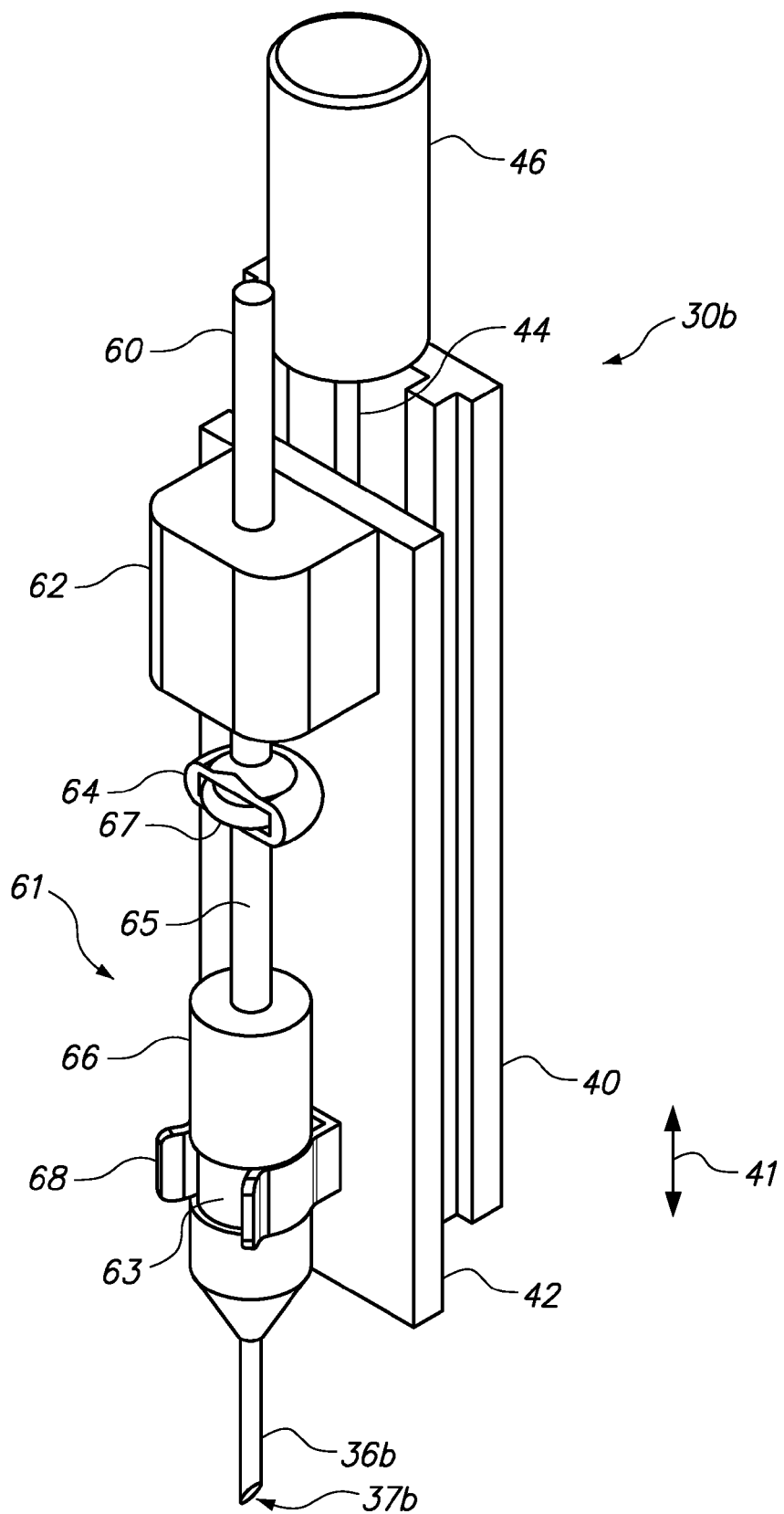
FIG. 3 is a partially schematic, perspective view of another embodiment of a delivery device carried in the actuator housing of the system of FIG. 1, and configured for transcutaneous delivery of a flowable therapeutic or cosmetic substance into body tissue.

FIG. 3 is a partially schematic, perspective view of another embodiment of a delivery tool assembly 30 (designated 30B), which may be mounted in the delivery tool housing 22 attached to the robotic arm of the robotic system 25. As with assembly 30A, the delivery tool assembly 30B includes an anchor plate 40 that is fixed to an inner wall of the delivery tool housing 22, and a delivery tool plate 42 that is movably coupled to the anchor plate 40 under the control of a motor 46. The delivery cannula 36 (designated as 36b) of delivery tool assembly 30B is the needle of a syringe assembly 61 that is removably coupled to the delivery tool plate 42. The syringe assembly 61 includes a barrel-shaped body 66 having an interior chamber, which may be pre-loaded (or otherwise loaded after attachment of the syringe assembly to the delivery assembly 30B) with a flowable therapeutic or cosmetic substance. The syringe body 66 has a slightly recessed mid-section 63 having an outer-diameter sized to be fixedly secured to the delivery tool plate 42 by a snap-fit clamp 68. In this manner, the syringe needle 36b may be advanced out of (or retracted into) the delivery tool housing 22 by movement the delivery tool plate 42 relative to the anchor plate 44, indicated by the two-way arrows 41.

The syringe assembly 61 further comprises a handle 67 attached to a plunger 65, which in turn is attached to a piston (not shown) positioned in the syringe body chamber as is conventional and well-known for alternately drawing a substance into the chamber through the distal cannula opening 37b, if the handle/plunger 67/65 are pulled back proximally relative to the syringe barrel 66, or dispensing a substance from the inner chamber out of the distal cannula opening 37b, if the handle/plunger 67/65 are pushed distally into the syringe body 66. The handle 67 fits into and is held by an actuator fitting 64. The delivery assembly 30B further comprises a linear motor 62 attached to the delivery tool plate 42, which controllably and precisely moves a push/pull rod 60 attached to the actuator fitting 64, to thereby move the syringe handle and plunger 67/65 relative to the syringe body 66 in order to dispense a desired quantity of the flowable substance from the syringe body chamber, out of distal cannula opening 36b, to a targeted tissue region.

During a procedure performed using the system 25 with the delivery tool assembly 30B to deliver (i.e., inject) precise doses of a therapeutic or cosmetic substance carried in the inner chamber of the syringe body 66 to specific targeted cutaneous, subcutaneous or intramuscular tissue regions, a system operator, an automated program, or a combination of each, directs the controller to maneuver the robotic arm 27 until the delivery cannula 36b is at a desired position and orientation proximate a targeted location on a patient's skin surface. Such movement is normally controlled, at least in part, through image-guidance based on images obtained from the one or more cameras 28 (as taught in the above-incorporated U.S. patent application Ser. Nos. 11/380,903 and 11/421,438). Once the delivery cannula 36b is in a desired position/orientation relative to the patient's skin surface, a system processor causes the motor 46 to move the delivery tool plate 42 relative to the anchor plate 40, to thereby cause the tissue-piercing distal end 37b of the delivery cannula 36b to puncture the skin surface and penetrate a desired depth into the tissue at the targeted location.

As with the use of delivery tool assembly 30A, movement of the delivery cannula 36b relative to the patient's skin surface can alternatively or additionally be accomplished by further movement of the robotic arm 27 relative to the patient's skin surface, with the depth of penetration depending on which tissue region(s) (i.e., epidermis, dermis, subcutaneous fat layer, intramuscular tissue region) the substance is to be injected into. Again, the actual depth of the respective tissue region boundaries may vary from patient to patient, and a particular desired penetration depth for given patient may be dependent on intradermal and subcutaneous images acquired by the one or more cameras 28 (or otherwise acquired by a different tissue imaging modality), from which the tissue layer depths may be determined. Once the cannula tip 37b is positioned at a desired depth, the system processor activates the motor 62 to thereby move the rod 60 and, thus, the syringe plunger 65, into to syringe body 66, to thereby dispense a desired quantity of the flowable therapeutic or cosmetic substance from the syringe body 66 into the tissue region.

Figure 4:
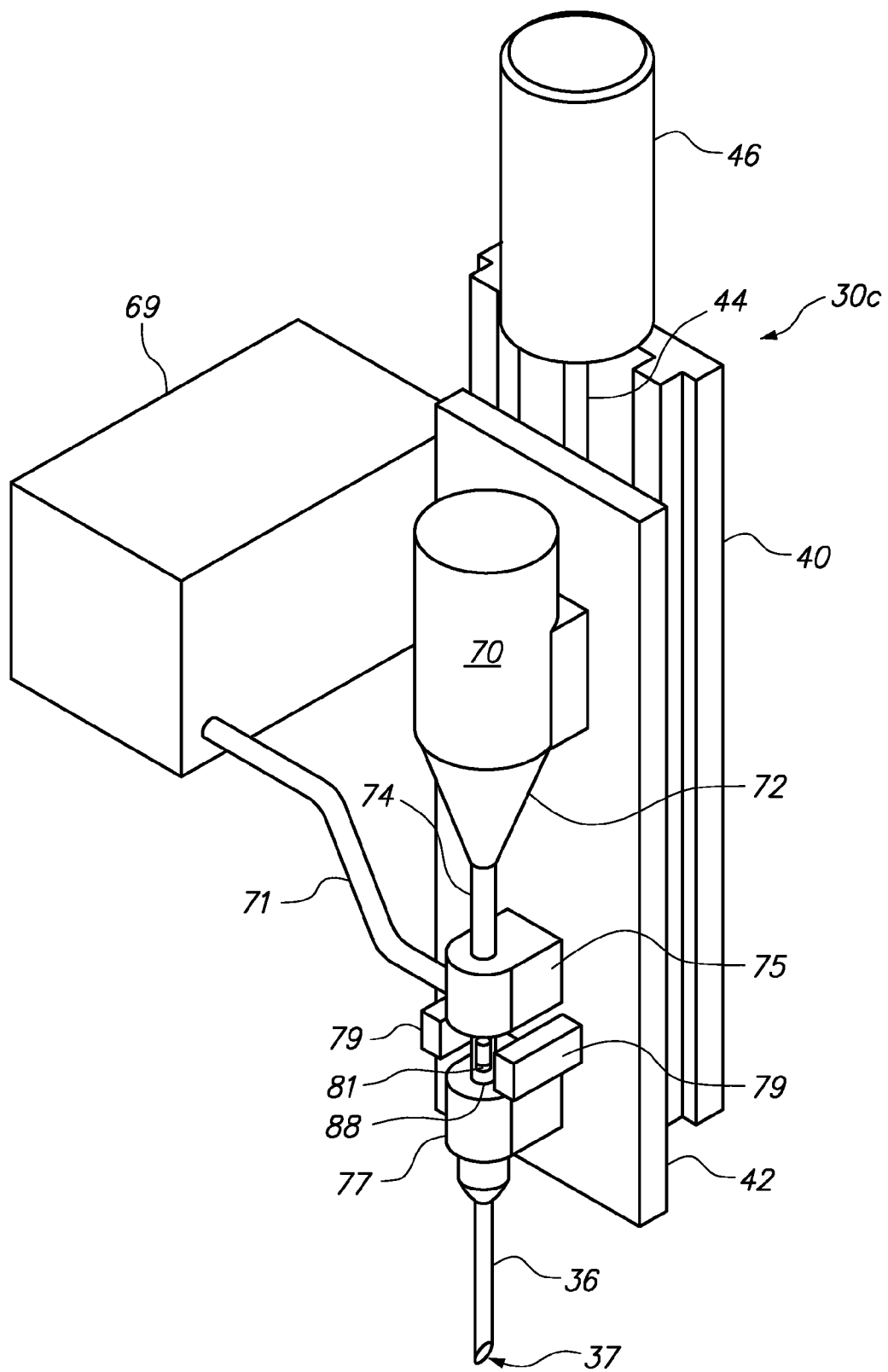
FIG. 4 is a partially schematic, perspective view of still another embodiment of a delivery device carried in the actuator housing of the system of FIG. 1, this one configured for transcutaneous delivery of solid or semi-solid aggregates, clumps or clusters, e.g., cellular material pellets into body tissue.

FIG. 4 is a partially schematic, perspective view of another embodiment of a delivery tool assembly 30 (designated 30C), which may be mounted in the delivery tool housing 22 of the robotic system 25, and is particularly configured for controlled delivery of solid or semi-solid (e.g., cellular material) pellets 81 into targeted body tissue through the delivery cannula 36. As with assemblies 30A and 30B, assembly 30C includes an anchor plate 40 fixed to an inner wall of the housing 22, and a delivery tool plate 42 movably coupled to the anchor plate 40 along a screw or similar longitudinal tack 44 relative to the anchor plate 40, controlled by a motor 46. A pellet container 70 is attached (or attachable) to the delivery tool plate 42, and has a funnel-shaped lower portion 72 tapering into an outlet 74. The pellet container outlet 74 is coupled to a control valve 75, which selectively and controllably allows passage of individual cellular matter pellets, i.e., one at a time, into a delivery chamber 88 when the valve 75 is opened by the system processor.

The presence of a pellet 81 in the delivery chamber 88 is detected by a sensor 79, which provides feedback to the processor to close the control valve 75 to prevent more than one pellet 81 at a time from entering into the delivery chamber 88. To deliver a pellet 81 positioned in the delivery chamber 88 through the distal end opening of the delivery cannula 36 and into a targeted tissue region, a delivery valve 77 is opened while the control valve 75 remains closed, and a source 69 of pressurized gas or fluid (e.g., air) is activated. The pressure source 69 is in communication with the delivery chamber 88, via a pressure supply line 71, thereby forcibly discharging the pellet 81 from the delivery chamber 88, through open valve 77, and out the open end 37 of the delivery cannula 36.

During a procedure performed using the system 25 with the delivery tool assembly 30C to deliver substantially precise quantities of the cellular matter pellets to specific targeted cutaneous, subcutaneous or intramuscular tissue regions, a system operator, an automated program, or a combination of each, directs the controller to maneuver the robotic arm 27 until the delivery cannula 36 is at a desired position and orientation proximate a targeted location on a patient's skin surface. Such movement is normally controlled, at least in part, through image-guidance based on images obtained from the one or more cameras 28 (as taught in the above-incorporated U.S. patent application Ser. Nos. 11/380,903 and 11/421,438). Once the delivery cannula 36 is in a desired position/orientation relative to the patient's skin surface, a system processor causes the motor 46 to move the delivery tool plate 42 relative to the anchor plate 40, to thereby cause the tissue-piercing distal end 37 of the delivery cannula 36 to puncture the skin surface and penetrate a desired depth into the tissue at the targeted location.

As with the use of delivery tool assemblies 30A and 30B, movement of the delivery cannula 36 relative to the patient's skin surface can alternatively or additionally be accomplished by further movement of the robotic arm 27 relative to the patient's skin surface, with the depth of penetration depending on which tissue region(s) (epidermis, dermis, subcutaneous fat layer, intramuscular tissue region) in which the pellets are to be delivered. Again, the actual depth of the respective tissue region boundaries may vary from patient to patient, and a particular desired penetration depth for given patient may be dependent on intradermal and subcutaneous images acquired by the one or more cameras 28 (or otherwise acquired by a different tissue imaging modality), from which the tissue layer depths may be determined. Once the cannula tip 37b is positioned at a desired depth, the system processor causes one or more pellets to be dispensed from the container into the tissue region.

By way of illustration, with reference to FIGS. 8A-7D, by image-guided maneuvering of the robotic arm 27, the tissue-piercing distal tip 37 of the delivery cannula 36 is positioned (and oriented) at targeted location 31 on a patient's skin surface 32 (shown in FIG. 8A). Thereafter, as indicated by arrow 1064 in FIG. 8B, the delivery cannula 36 punctures and penetrates into the skin surface 32, through the epidermis 100 and dermis 102, until the cannula distal tip 37 reaches a desired depth of penetration in the subcutaneous fat layer 104. Thereafter, as shown in FIG. 8C, a metered dose of cellular matter pellets 81 are released through the delivery cannula 36 into the subcutaneous tissue 104. In the illustrated example, the pellets 81 continue to be released from the cannula 36 into the subcutaneous fat layer 104, as the cannula 36 is withdrawn, as indicated by arrow 108 in FIG. 8D.

Figure 5:
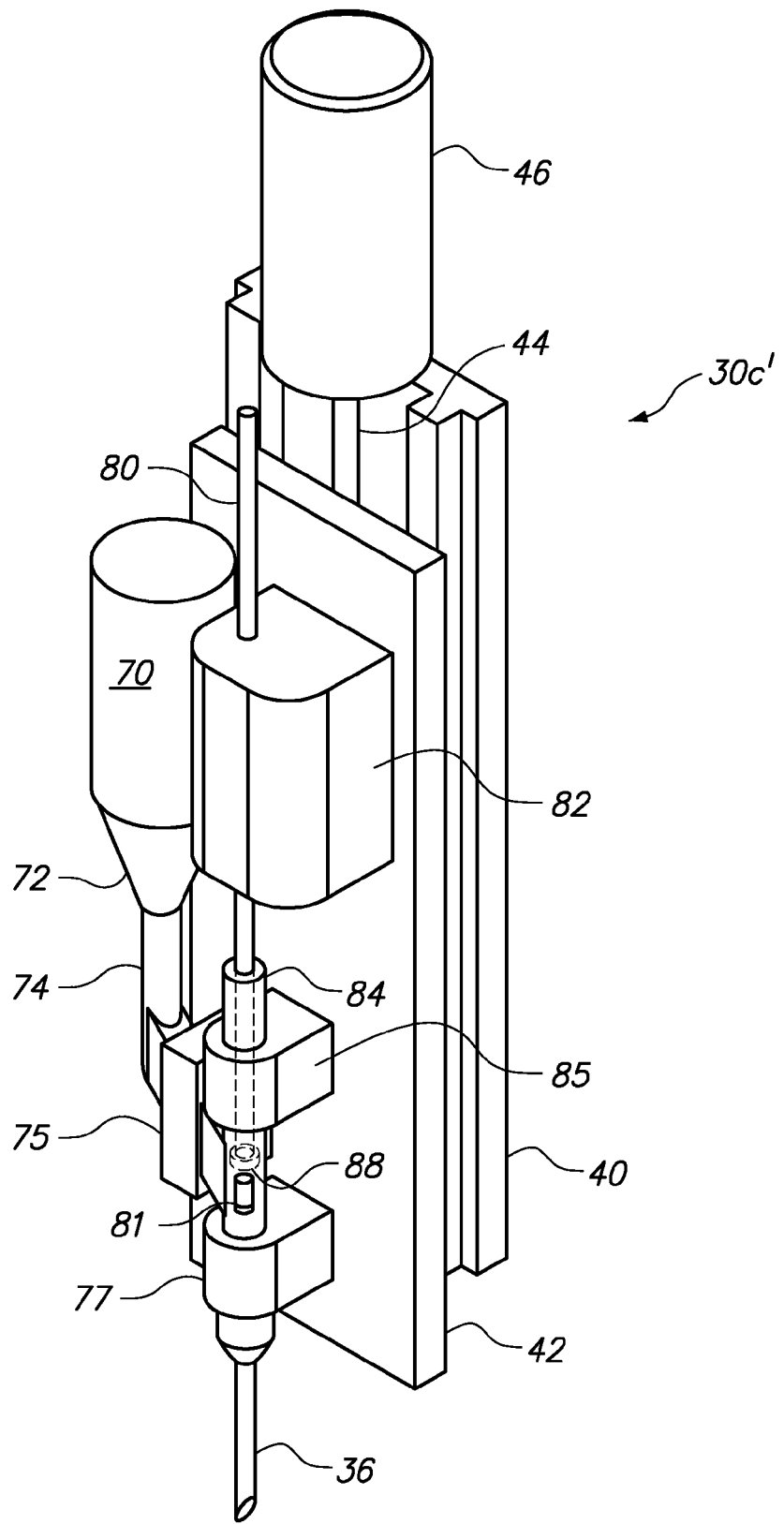
FIG. 5 is a partially schematic, perspective view of an alternate embodiment of the delivery device of FIG. 4.

FIG. 5 is a partially schematic, perspective view of an alternate embodiment of the delivery tool assembly 30C (designated 30C'), which may be mounted in the delivery tool housing 22 of the robotic system 25. The delivery tool assembly 30C' is substantially identical to the delivery tool assembly 30C, except that (i) cellular matter pellets from the pellet container 70 are loaded laterally into the delivery chamber 88 via the control valve 75, and (ii) rather than using a pressurization source, pellets 81 in the delivery chamber 88 are dispensed through the delivery valve 77 by an obturator 80, which is controlled by a linear motor 82 fixed to the delivery tool plate 72. In the illustrated assembly 30C', a guide 85 fixed to the delivery tool plate, and sleeve 84 are provided to stabilize and center to obturator.

By way of illustration, during a procedure performed using the system 25 and delivery tool assembly 30C to deliver cellular matter pellets 81 carried in the container 70 to targeted tissue regions in a patient, the delivery cannula 36 is positioned at a desired depth in a respective targeted tissue region, and the system processor opens the delivery valve 77 and activates the linear motor 82 to move the obturator 80 distally to thereby displace a respective pellet 81 from the delivery chamber 88, through the open delivery valve 77, and out the distal end opening 37 of the delivery cannula 36 into the targeted tissue.

As noted above, embodiments of the robotic system 25 employing any of the foregoing delivery tool assemblies 30A, 30A', 30B, 30C and 30C' (or an alternative delivery tool assembly) may be used for delivery of a therapeutic or cosmetic substance into (or proximate) the cutaneous or subcutaneous tissue of existing hair follicles in a body surface of a patient. In such embodiments, the robotic arm 27 may be maneuvered under image guidance to position the delivery cannula 36 proximate an existing (e.g., a "miniaturized") hair follicle. A tissue-piercing distal end 37 of the delivery cannula 36 then punctures and penetrates the skin surface to a desired depth into the cutaneous or subcutaneous tissue at least partially surrounding (or otherwise adjacent to) the targeted hair follicle. A therapeutic or cosmetic substance is then delivered to the cutaneous and/or subcutaneous tissue from the delivery cannula.

As with "non-hair related" applications and procedures, the therapeutic or cosmetic substance may be in a readily flowable or non-flowable form, and may comprise substances such as stem cells, hair inductive dermal papilla cells; pharmaceuticals that effect hair growth, such as minoxidil, finasteride, androgens/anabolic steroids, estrogen, phenytoin, retinoids, cyclosporine and other small chemical compounds under development for hair growth; and peptides/proteins such as Growth Hormone (GH), or a hair follicle growth factor, such as autologous platelet plasma.

The robotic arm 27 may be repeatedly maneuvered to reposition the delivery cannula 36 a number of existing hair follicles during a single procedure. In some embodiments, the distal end of delivery device at least partially surrounds the respective targeted hair follicle as it penetrates the skin surface. In other embodiments, the delivery device axis forms an angle with the targeted hair follicle as the deliver device punctures and penetrates the skin surface. In some embodiments, the therapeutic or cosmetic substance is delivered at multiple discrete locations in the cutaneous and/or subcutaneous tissue of, or proximate to, the targeted hair follicle(s). Also, it may be possible to position the cannula 36 to substantially surround multiple (closely located) hair follicles during a single penetrating motion. In some embodiments, the automated system comprises a user interface that allows a system operator to input instructions relating, by way of non-limiting example, to at least one of a location, orientation and penetration depth of the distal end of the delivery device relative to the targeted hair follicle(s). Additionally or alternatively, the user interface may allow a system operator to input instructions relating to a type, a quantity, or both, of the therapeutic or cosmetic substance to be delivered.

By way of illustration, with reference to FIGS. 9A-9D, by image-guided maneuvering of the robotic arm 27, the tissue-piercing distal tip 37 of the delivery cannula 36 is positioned (and oriented) to surround a targeted hair follicle 112 that extends from a base 114 located in the subcutaneous fat layer 104, through the dermis 102 and out the epidermis 100, respectively on a patient's skin surface 32 (shown in FIG. 9A). Thereafter, as indicated by arrow 115 in FIG. 9B, the delivery cannula 36 punctures and penetrates into the skin surface 32, through the epidermis 100 and dermis 102, until the cannula distal tip 37 reaches a desired depth of penetration in the subcutaneous fat layer 104 proximate the base 114 of the hair follicle 112.

Notably, the beveled tip 37 of the cannula 36 does not completely enclose the hair follicle 112, so as to minimize the chance that the follicle 112 will be cannulated and removed from the skin surface 32 as the cannula 36 is withdrawn. As shown in FIG. 9C, a metered dose of a therapeutic or cosmetic substance 125 is released through the delivery cannula 36 into the subcutaneous tissue 104 surrounding or substantially surrounding the hair follicle 112, as the cannula is pulled back from its deepest point of penetration (indicated by arrow 117). In the illustrated example, the substance 125 continues to be released from the cannula 36 into the tissue surrounding or substantially surrounding the hair follicle 112, as the cannula 36 is withdrawn from the subcutaneous fat layer 104 and back through the dermis 102 (indicated by arrow 118 in FIG. 9D).

By way of further illustration, with reference to FIGS. 10A-10D, the tissue-piercing distal tip 37 of the delivery cannula 36 is positioned (and oriented) to surround a targeted hair follicle 112 that extends from a base 114 located in the subcutaneous fat layer 104, through the dermis 102 and out the epidermis 100, respectively on a patient's skin surface 32 (shown in FIG. 10A). Thereafter, as indicated by arrow 127 in FIG. 10B, the delivery cannula 36 punctures and penetrates into the skin surface 32, through the epidermis 100 and dermis 102, until the cannula distal tip 37 reaches a desired depth of penetration in the subcutaneous fat layer 104 proximate the base 114 of the hair follicle 112. Again, the beveled tip 37 of the cannula 36 does not completely enclose the hair follicle 112, so as to minimize the chance that the follicle 112 will be cannulated and removed from the skin surface 32 as the cannula 36 is withdrawn. As shown in FIG. 10C, a metered number of one or more cellular matter pellets 81 are released through the delivery cannula 36 into the subcutaneous tissue 104 proximate the hair follicle 112, as the cannula is pulled back from its deepest point of penetration (indicated by arrow 128). In the illustrated example, the pellets 81 continue to be released from the cannula 36 into the tissue proximate the hair follicle 112, as the cannula 36 is withdrawn from the subcutaneous fat layer 104 and back through the dermis 102 (indicated by arrow 129 in FIG. 10D).

Figures 11A, 11B, 11C:
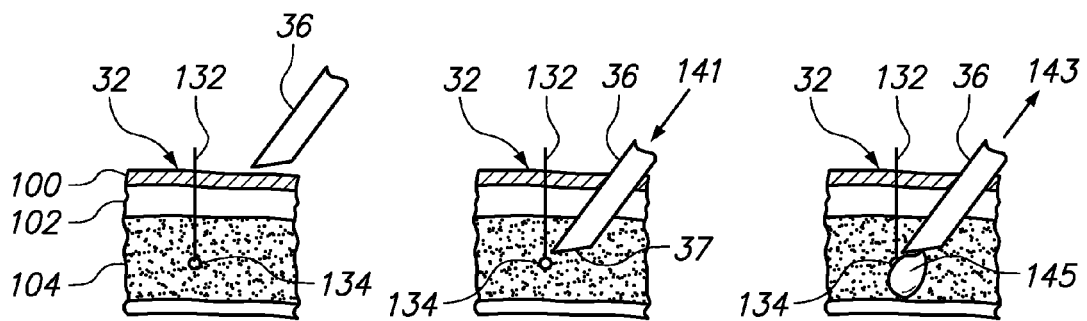
FIGS. 11A-C are simplified, partially cut-away views of a procedure in which a delivery device delivers a flowable substance to subcutaneous tissue proximate an existing hair follicle.

By way of still further illustration, with reference to FIGS. 11A-11C, the tissue-piercing distal tip 37 of the delivery cannula 36 may alternately be positioned (and oriented) to approach a targeted hair follicle 132 from an angle, which extends from a base 134 located in the subcutaneous fat layer 104, through the dermis 102 and out the epidermis 100, respectively on a patient's skin surface 32 (shown in FIG. 11A). Thereafter, as indicated by arrow 141 in FIG. 11B, the delivery cannula 36 punctures and penetrates into the skin surface 32, through the epidermis 100 and dermis 102, until the cannula distal tip 37 reaches a location and depth of penetration in the subcutaneous fat layer 104 adjacent the base 134 of the hair follicle 132. As shown in FIG. 11C, a metered dose of a therapeutic or cosmetic substance 145 is released through the delivery cannula 36 into the subcutaneous tissue 104 proximate the base 134 of the hair follicle 134, as the cannula 136 is pulled back from its deepest point of penetration (indicated by arrow 143).

Figure 12:
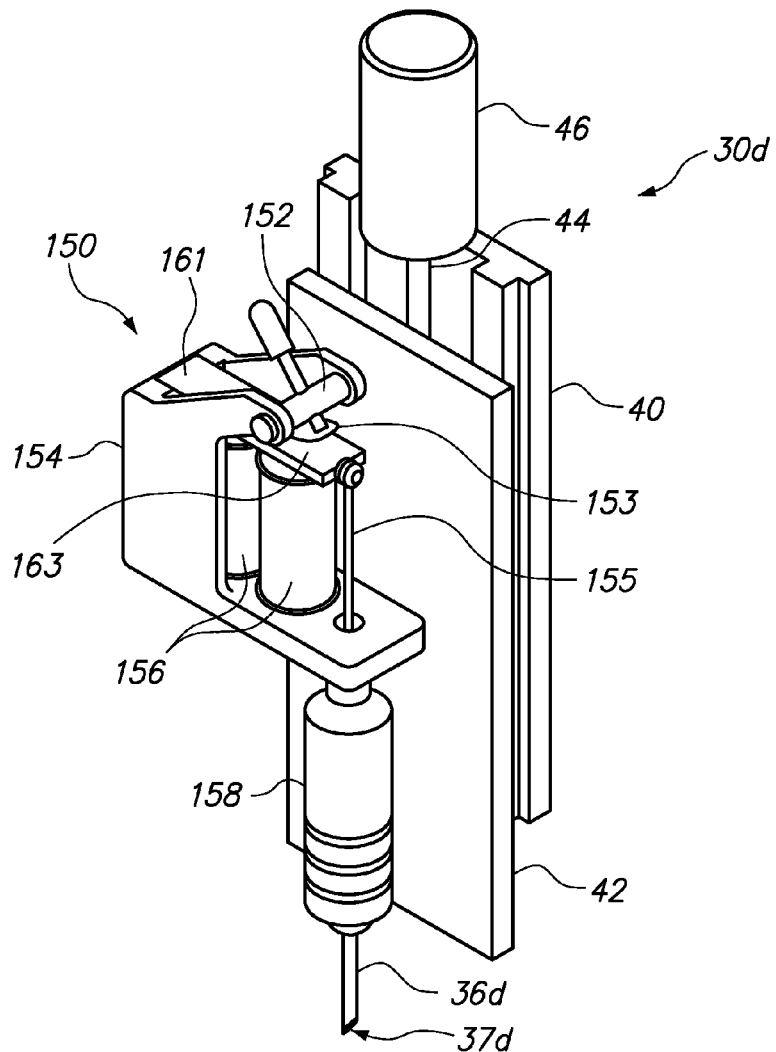
FIG. 12 is a partially schematic, perspective view of yet another embodiment of a delivery device carried in the actuator housing of the system of FIG. 1, and configured for intradermal delivery of pigment ink for generating face and other body surface tattoos.

FIG. 12 is a partially schematic, perspective view of yet another delivery tool assembly 30 (designated 30D), which may be mounted in the delivery tool housing 22 of the robotic system 25, and is particularly configured for controlled delivery of pigment ink into targeted dermis tissue through the delivery cannula 36 for generating tattoos. As with assemblies 30A-C, delivery tool assembly 30D includes an anchor plate 40 fixed to an inner wall of the housing 22, and a delivery tool plate 42 movably coupled to the anchor plate 40 along a screw or similar longitudinal tack 44 relative to the anchor plate 40, controlled by a motor 46. A conventional tattoo machine 150 (with slight modifications) is fixed to the delivery tool plate 42, wherein the delivery cannula 36 comprises the tissue piercing needle (designated 36d) of the tattoo machine 150.

Advantageously, operation of the tattoo machine 150 is under common control as the robotic system 25, wherein the tissue piercing tip 37 of the delivery cannula 36 may be positioned and oriented relative to a targeted skin surface as described above. Movement of the delivery cannula 36 relative to the skin surface may be accomplished by relative movement of the robotic arm 27 (under image guidance), the tool plate 42, or a combination of each. Preferably, however, those actuations are made only for positioning the cannula tip 37 at the skin surface (akin to a conventional human "tattoo artist" holding a tattoo machine in position at the skin surface). Actual penetration of the skin surface and delivery of the pigment ink is performed by the tattoo machine 150, which is under common control with the robotic system 25. A summary description follows of the main components and operation of the tattoo machine 150, with an attribution to http://en.wikipedia.org/wiki/Tattoo machine as the source of this information.

Generally, the tattoo machine 150 employs an alternating current charge that causes electromagnets 156 to pull downward on an armature bar 163, which in turn pulls down on a reciprocating rod 155 that drives the delivery cannula 36d. The downward motion of the bar 163 also disconnects the circuit and allows an upward force of a spring ("armature spring") 161 to pull the armature bar 163 back to its initial position. More particularly, alternating current power is conducted in one direction through a pair of electromagnetic coils 156 mounted on a conductive frame 154, to an adjustable contact screw 152; and in another direction through the frame 154 to a contact spring 153, via the armature spring 161, by way of example, the frame 154 can be made of a conductive material such as iron, brass or copper and plastic bushings at the contact points are to be used to isolate the current from the frame. Alternatively, the frame may be made of a non-conductive material, with a yoke provided to connect the coils to the wiring for completing a circuit. Current flowing between the contact screw 152 and the contact spring 153, completes the circuit, thereby causing the electromagnetic coils 156 to pull down on the armature bar 163, which in turn causes the reciprocating rod 155 and (in turn) delivery cannula 36 to move with it, such that the tissue piercing distal end 37d of the delivery cannula 36d may puncture and penetrate the skin surface. Once the circuit is broken, the armature spring 161 exerts an upward force, pulling the reciprocating rod with it, causing the cannula end 37d to be pulled back out of the skin surface. This motion also cause the circuit to again close with the contact made between the contact spring 153 and adjustable screw 152. The process may be repeated at a relatively fast rate, e.g., between 80 and 150 times a second. A capacitor (not shown) may be provided to regulate current flow through the tattoo machine 150. An ink reservoir 158 is coupled to the respective reciprocating rod 155 and delivery cannula 36d, and provides a source of pigmentation ink in fluid communication with the delivery cannula 36d.

It should be appreciated that the illustrated tattoo gun 150 is provided by way of example and not limitation, and is essentially a variation of a currently available hand-held model that has been mounted on the delivery tool plate 42 in the delivery tool housing 22 of the robotic system 25. Many variations and alternatives are available and will be apparent to those skilled in the art for providing a reciprocating delivery cannula 36d for controlled delivery of the pigment (tattoo) ink, which may be advantageously positioned (and held) by the robotic arm 27 and/or movable tool plate 42.

The forgoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. By way of non-limiting example, it will be appreciated by those skilled in the art that the invention is not limited to the use of a robotic system, and that other automated systems and apparatus may be used for positioning and actuating the respective delivery and removal end-effectors and components disclosed herein.

What is claimed is:

1. An automated system for transcutaneous delivery of a therapeutic or cosmetic substance into a cutaneous, subcutaneous or intramuscular tissue region, comprising:
   an automated arm;
   a delivery device mounted on the automated arm;
   one or more cameras mounted on the automated arm;
   a processor configured to receive and process images acquired by the one or more cameras; and
   a controller operatively associated with the processor and configured to maneuver the automated arm based, at least in part, on images acquired by the one or more cameras and processed by the processor,
   wherein the automated arm is configured to be maneuverable to position the delivery device proximate a targeted location on a patient's skin surface, and one or both of the processor and controller is configured to cause (i) a distal end of the delivery device to puncture the skin surface at the targeted location and penetrate into a tissue to generate a tissue penetration track in the tissue, and (ii) a controlled delivery through the delivery device of a therapeutic or cosmetic substance into the tissue at multiple locations along the tissue penetration track while retracting the delivery device from the tissue penetration track.

2. The system of claim 1, wherein the automated system is a robotic system, and the automated arm is a robotic arm.

3. The system of claim 2, further comprising a container carried on the robotic arm, wherein the therapeutic or cosmetic substance is a flowable substance supplied from the container.

4. The system of claim 3, wherein the container is removably coupled to the robotic arm.

5. The system of claim 2, further comprising a plurality of reservoirs carried on the robotic arm, each reservoir containing a respective therapeutic or cosmetic substance, wherein the delivery device may be selectively coupled to a respective one of the plurality of reservoirs.

6. The system of claim 1, wherein the delivery device comprises a cannula or a needle removably coupled to the automated arm.

7. The system of claim 1, wherein the images include intradermal or subcutaneous images.

8. The system of claim 1, wherein the therapeutic or cosmetic substance comprises inductive dermal sheath cells and/or inductive dermal papilla cells.

9. The system of claim 1, further comprising a user interface that allows a system operator to input instructions relating to one or more of a location of the delivery device, an orientation of the delivery device, a penetration depth of the delivery device, a type of the therapeutic or cosmetic substance, or a quantity of the therapeutic or cosmetic substance to be delivered into a targeted tissue region.

10. The system of claim 1, the therapeutic or cosmetic substance comprising cellular matter pellets stored in a container carried on the automated arm, the system comprising means for dispensing from the container and delivering a controlled number of pellets to the target tissue region.

11. The system of claim 10, wherein the dispensing and delivering means comprises a source of pressurization.

12. The system of claim 10, wherein the one or both of the processor and controller further configured to cause one or more cellular matter pellets to be dispensed from the container into the target tissue region once the delivery device is positioned at a desired depth.

13. The system of claim 1, wherein the therapeutic or cosmetic substances is selected from the group comprising hair growth cells, minoxidil, finasteride, androgens, anabiolic steroids, estrogen, phenytoin, retinoids, cyclosporine, Growth Hormone (GH), autologous platelet plasma, fat cells, syaluronic acis, collagen, clostridium botulinum (Botox®), natural polymer synthetic polymer, anesthetics, saline solution, and calcium particles.

14. The system of claim 1, wherein the therapeutic or cosmetic substance comprises one or more cellular matter pellets, the system further comprising a container, a delivery chamber, and a valve, wherein the valve allows passage of a controlled number of pellets from the container into the delivery chamber when the chamber is opened.

15. The system of claim 1, wherein the one or both of the processor and controller configured to cause the controlled delivery of the therapeutic or cosmetic substance while the delivery device is being withdrawn from the tissue penetration track.

16. The system of claim 1, wherein the therapeutic or cosmetic substance aids in inducing hair growth and/or retention of hair.

17. The system of claim 1, wherein the targeted location comprises one or more hair follicles and an axis of the delivery device forms an angle with a hair follicle of the one or more hair follicles as the delivery device punctures and penetrates the skin surface.

18. The system of claim 17, wherein a distal end of the delivery device at least partially surrounds the hair follicle as the delivery device penetrates the skin surface.

19. The system of claim 17, wherein the therapeutic or cosmetic substance is delivered at multiple discrete locations in the cutaneous or subcutaneous tissue proximate the hair follicle.

20. An automated system for transcutaneous delivery of a therapeutic or cosmetic cellular or pharmacological matter into a cutaneous, subcutaneous or intramuscular tissue region, comprising:
an automated arm;
a cellular or pharmacological matter delivery device carried by the automated arm;
one or more cameras;
a processor configured to receive and process images acquired by the one or more cameras; and
a controller operatively associated with the processor and configured to maneuver the automated arm based, at least in part, upon images acquired by the one or more cameras and processed by the processor;
wherein the automated arm is configured to be maneuverable to position the cellular or pharmacological matter delivery device proximate a targeted location on a patient's body surface, and one or both of the processor and controller arc is configured to cause a controlled delivery of a therapeutic or cosmetic cellular or pharmacological matter at multiple locations along a tissue penetration track while the delivery device is being withdrawn from the tissue penetration track, the tissue penetration track being generated as the delivery device punctures the body surface at the targeted location and penetrates into the tissue.

21. The system of claim 20, wherein the cellular or pharmacological matter is in the form of a flowable substance.

22. The system of claim 20, wherein the cellular or pharmacological matter is in the form of a flowable substance, the system further comprising a plurality of reservoirs carried on the automated arm, each reservoir containing a respective therapeutic or cosmetic cellular or pharmacological matter, wherein the delivery device may be selectively coupled to a respective one of the plurality of reservoirs.

23. The system of claim 20, wherein the therapeutic or cosmetic cellular or pharmacological matter comprises matter that induces hair growth and/or retention of hair.

24. The system of claim 20, further comprising a user interface that allows a system operator to input instructions relating to one or more of: location of the delivery device, an orientation of the delivery device, a penetration depth of the cellular or pharmacological matter delivery device, a type of the cellular or pharmacological matter, or a quantity of the cellular or pharmacological matter.

25. The system of claim 20, wherein the therapeutic or cosmetic cellular or pharmacological matter comprises cellular matter pellets.

26. The system of claim 25, wherein the cellular matter pellets comprise inductive dermal sheath cells and/or inductive dermal papilla cells.

27. The system of claim 20, wherein the automated system is a robotic system, and the automated arm is a robotic arm.

28. An automated system for transcutaneous delivery of a therapeutic or cosmetic substance into a cutaneous, subcutaneous or intramuscular tissue region, comprising:
an automated arm;
a delivery device carried by the automated arm;
one or more cameras carried by the automated arm;
a processor configured to receive and process images acquired by the one or more cameras; and
a controller operatively associated with the processor and configured to maneuver the automated arm based, at least in part, on images acquired by the one or more cameras;
wherein the automated arm is maneuverable to position the delivery device proximate a targeted location on a patient's skin surface, and one or both of the processor and controller configured to cause (i) a distal end of the delivery device to puncture the skin surface and penetrate into tissue at the targeted location, and (ii) a controlled delivery through the delivery device of a therapeutic or cosmetic substance into the tissue; and
wherein the therapeutic or cosmetic substance comprises one or more cellular matter pellets, the system further comprises a container, a delivery chamber, a sensor, and a first valve, wherein the first valve allows passage of a controlled number of pellets from the container into the delivery chamber and the sensor provides information to control the first valve to prevent more than the controlled number of pellets entering the delivery chamber at a time, the system further comprises a second valve and the system is configured to allow a predetermined number of pellets to be delivered from the delivery chamber to the tissue when the second valve is open.

29. The system of claim 28, wherein the one or more cellular matter pellets comprise inductive dermal sheath cells and/or inductive dermal papilla cells.

30. The system of claim 28, further comprising a source of pressurization in communication with the delivery chamber, the source of pressurization being activated when the first valve is closed to cause one or more of the predetermined number of pellets in the delivery chamber to be delivered to the target tissue region.

31. The system of claim 28, wherein the pellets are metered out of the delivery chamber at a constant dispensing rate as the delivery device is retracted out of the tissue.

* * * * *

UNITED STATES PATENT AND TRADEMARK OFFICE
CERTIFICATE OF CORRECTION

PATENT NO. : 7,922,688 B2
APPLICATION NO. : 11/621087
DATED : April 12, 2011
INVENTOR(S) : Bodduluri et al.

Page 1 of 1

It is certified that error appears in the above-identified patent and that said Letters Patent is hereby corrected as shown below:

In the Claims

Column 23, line 14, in Claim 13, replace "subsances" with --substance--.

Column 23, line 65, in Claim 20, replace "controller arc is" with --controller is--.

Signed and Sealed this
Twenty-sixth Day of November, 2013

Margaret A. Focarino
*Commissioner for Patents of the United States Patent and Trademark Office*